US011666262B2

(12) United States Patent
Yamagata

(10) Patent No.: US 11,666,262 B2
(45) Date of Patent: Jun. 6, 2023

(54) INFORMATION DISPLAY DEVICE, BIOLOGICAL SIGNAL MEASUREMENT SYSTEM AND COMPUTER-READABLE RECORDING MEDIUM

(71) Applicant: Hideaki Yamagata, Kanagawa (JP)

(72) Inventor: Hideaki Yamagata, Kanagawa (JP)

(73) Assignee: RICOH COMPANY, LTD., Tokyo (JP)

(*) Notice: Subject to any disclaimer, the term of this patent is extended or adjusted under 35 U.S.C. 154(b) by 583 days.

(21) Appl. No.: 16/489,837

(22) PCT Filed: Jan. 31, 2018

(86) PCT No.: PCT/JP2018/003306
§ 371 (c)(1),
(2) Date: Aug. 29, 2019

(87) PCT Pub. No.: WO2018/168235
PCT Pub. Date: Sep. 20, 2018

(65) Prior Publication Data
US 2020/0060564 A1    Feb. 27, 2020

(30) Foreign Application Priority Data
Mar. 17, 2017 (JP) .............................. JP2017-053396

(51) Int. Cl.
*A61B 5/245* (2021.01)
*A61B 5/0245* (2006.01)
(Continued)

(52) U.S. Cl.
CPC ............ *A61B 5/245* (2021.01); *A61B 5/0245* (2013.01); *A61B 5/369* (2021.01); *A61B 5/7203* (2013.01);
(Continued)

(58) Field of Classification Search
CPC .... A61B 5/7425; A61B 5/7203; A61B 5/0245; G06V 20/46; G10K 11/175
See application file for complete search history.

(56) References Cited

U.S. PATENT DOCUMENTS 6,067,467 A * 5/2000 John .................... A61B 5/4821
600/544
9,693,735 B2   7/2017 Ishiguro et al.
(Continued)

FOREIGN PATENT DOCUMENTS

CA         2812783 A1    6/2013
CN         1495703 A     5/2004
(Continued)

OTHER PUBLICATIONS

Tutorial 13: Artifact cleaning with SSP 2015, https://web.archive.org/web/20151229180343/http://neuroimage.usc.edu/brainstorm/Tutorials/ArtifactsSsp (Year: 2015).*
(Continued)

*Primary Examiner* — Oommen Jacob
(74) *Attorney, Agent, or Firm* — Harness, Dickey & Pierce, P.L.C.

(57) ABSTRACT

An information display device includes a component extraction unit configured to extract a requested component from multiple given waveforms that are cut out of multiple signal waveforms based on biological signals that are detected; and a noise component selection unit configured to accept selecting, as a noise component, a result of the extracting from multiple results of the extracting by the component extraction unit, and the noise component selection unit displays the multiple results of the extracting by the component extraction unit and times at which the specific waveforms occur.

20 Claims, 26 Drawing Sheets

(51) Int. Cl.
  *A61B 5/00* (2006.01)
  *G10K 11/175* (2006.01)
  *A61B 5/369* (2021.01)
  *G06V 20/40* (2022.01)

(52) U.S. Cl.
  CPC .......... *A61B 5/7239* (2013.01); *A61B 5/7425* (2013.01); *G06V 20/46* (2022.01); *G10K 11/175* (2013.01)

(56) References Cited

U.S. PATENT DOCUMENTS

| | | | |
|---|---|---|---|
| 10,959,656 B2* | 3/2021 | Kanayama | A61B 5/7425 |
| 2013/0109996 A1* | 5/2013 | Turnbull | A61B 5/7203 |
| | | | 600/544 |
| 2013/0138010 A1* | 5/2013 | Nierenberg | A61B 5/291 |
| | | | 600/544 |
| 2014/0195202 A1 | 7/2014 | Ishiguro et al. | |
| 2015/0261936 A1 | 9/2015 | Zhou et al. | |
| 2018/0268588 A1 | 9/2018 | Shinohara et al. | |
| 2019/0087996 A1 | 3/2019 | Shinohara et al. | |
| 2020/0060564 A1* | 2/2020 | Yamagata | A61B 5/369 |

FOREIGN PATENT DOCUMENTS

| | | |
|---|---|---|
| CN | 101152075 A | 4/2008 |
| CN | 101189570 A | 5/2008 |
| CN | 103488661 A | 1/2014 |
| CN | 103908248 A | 7/2014 |
| CN | 113496770 A | 10/2021 |
| JP | H10-005186 | 1/1998 |
| JP | H11-104101 A | 4/1999 |
| JP | 2001-126264 A | 5/2001 |
| JP | 3228703 | 9/2001 |
| JP | 2004-216184 | 8/2004 |
| JP | 2006-314688 | 11/2006 |
| JP | 2009-195571 | 9/2009 |
| JP | 2013-208368 A | 10/2013 |
| JP | 2019-111377 | 7/2019 |
| WO | WO-2005/046483 A1 | 5/2005 |

OTHER PUBLICATIONS

Tutorial 7:Event markers, https://web.archive.org/web/20160416081736/http://neuroimage.usc.edu/brainstorm/Tutorials/EventMarkers (Year: 2016).*

Brainstorm: Imaging neural activity at the speed of brain , https://www.youtube.com/watch?v=30eFJUrRcN4 (Year: 2015).*
Chinese Office Action and English translation thereof dated Aug. 3, 2021.
Francois Tadel, Elizabeth Bock, John C Mosher, Sylvain Baillet, "Tutorial 13: Artifact cleaning with SSP", Brainstorm Tutorials, Nov. 6, 2015(Nov. 6, 2015), XP002780470, Retrieved from the Internet: URL:http://web.archive.org/web/20151229180343/, http://neuroimage.usc.edu/brainstorm/Tutorials/ArtifactsSsp#expand XP002780470, [retrieved on Apr. 24, 2018], the whole document.
Francois Tadel, Sylvain Baillet, Anne-Sophie Dubarry, "MEG and EEG analysis with Brianstorm", Brainstorm, Dec. 2015 (Dec. 2015), XP002780471, Retrieved from the Internet: URL:http://neuroimage.usc.edu/brainstorm/WorkshopGrenoble2015?action=AttachFile&do=get&target=grenoble2015_slides.pdf [retrieved on Apr. 24, 2018], Slides 16, 18-21:Artifact correction, Slide 23: Epoching.
Fabrizio Esposito, Rainer Goebel, "EEG/MEG Temporal Independent Component Analysis", BrainVoyager QX v2.8 UsersGuide, Dec. 4, 2014 (Dec. 4, 2014), XP002780472, Retrieved from the Internet: URL:https://web.archive.org/web/20141204223025/http://www.brainvoyager.com/bvqx/doc/UsersGuide/EMEGSuite/EEMEGTemporalIndependentComponentsAnalysis.html [retrieved on Apr. 24, 2018], the whole document.
Francois Tadel, Elizabeth Bock, "SSP Cookbook", Brainstorm Tutorials, Aug. 2, 2016 (Aug. 2, 2016), XP002780473, Retrieved from the Internet: URL:http://neuroimage.usc.edu/brainstorm/Tutorials/SSPCookbook [retrieved on Apr. 24, 2018], the whole document.
Francois Tadel, Elizbeth Bock, John C Mosher, Sylvain Baillet, "C2. Detect and remove artifacts", Brainstorm Tutorials, Jul. 28, 2016 (Jul. 28, 2016), XP002780474, Retrieved from the Internet: URL:http://neuroimage.usc.edu/brainstorm/Tutorials/TutRawSsp [retrieved on Apr. 24, 2018], the whole document.
International Search Report dated May 15, 2018 in PCT/JP2018/003306 filed Jan. 31, 2018.
CN Office Action dated Mar. 11, 2022 in Chinese Application No. 201880018268.4.
C. Musser et al. 'Computer-assisted ECG Interpretation for Confirmation of Premature Atrial Complexes' *Journal of Electrocardiology*, vol. 34, 2001, pp. 197-203.
EP Office Action for corresponding European Patent Application No. 18706580.0 dated Jun. 28, 2022.
Onton Julie: "Data preprocessing and epoching", EEGLAB Workshop III, Nov. 15-18, 2006, Singapore, Jan. 1, 2006 (Jan. 1, 2006), pp. 1-36, XP055933032, Retrieved from the Internet: URL:https://sccn.ucsd.edu/eeglab/workshop06/handout/Practicum_ 1_data_import_epoch.pdf.

* cited by examiner

| | | Annotation List ▼ | | | |
|---|---|---|---|---|---|
| ☑ Show Markup on wave ———————— 180a | | | | | |
| No. | File | Time | Event | MEMO | Cluster |
| 2 ☐ | 001 | 00:09:30 🔥 | | normal spike | B |
| 1 ☐ | 001 | 00:05:00 🔥 | | strong spike | A |
| 0 ☐ | 000 | 00:00:00 🔥 | | Dr.memo | A |

Exit Measurement

180

INFORMATION DISPLAY DEVICE, BIOLOGICAL SIGNAL MEASUREMENT SYSTEM AND COMPUTER-READABLE RECORDING MEDIUM

TECHNICAL FIELD

The present invention relates to an information display device, a biological signal measurement system and a computer-readable recording medium.

BACKGROUND ART

A magneto-encephalograph (MEG) is an apparatus that examines brain functions by measuring weak magnetic fields that are generated by neural activities in a brain.

When magnetic fields are measured with a MEG, living-body dependent noises, such as magnetic fields generated by the heart, may be mixed. Thus, some technologies to remove noises mixed in MEG signals have been disclosed.

PTL 1 discloses a technology to remove a noise mixed in a MEG signal, with a device dedicated to measuring cardiac magnetic fields, by analyzing magnetic field waveforms and thus detecting the time of occurrence of the noise and then subtracting a noise signal from the original magnetic field signal.

SUMMARY OF INVENTION

Technical Problem

The conventional technology, however, uses the waveforms of the cardiac magnetic fields obtained from the device dedicated to measuring cardiac magnetic fields and thus, when magnetic field signals obtained with a MEG are measured, it is difficult to clearly distinguish waveforms of magnetic fields that are generated by the heart that are mixed as noises. Furthermore, the conventional technology requires an external device for synchronization with occurrence of noise and this complicates the device configuration.

In view of the above-described circumstances, there is a need to provide an information display device, a biological signal measurement system and a computer-readable recording medium having a program enabling extraction of a noise signal without fail from a complicated signal in which a signal to be acquired and the noise signal are mixed and enabling confirmation that the noise removal process is optimum.

Solution to Problem

According to an embodiment, an information display device includes a component extraction unit configured to extract a requested component from multiple given waveforms that are cut out of multiple signal waveforms based on biological signals that are detected; and a noise component selection unit configured to accept selecting, as a noise component, a result of the extracting from multiple results of the extracting by the component extraction unit, and the noise component selection unit displays the multiple results of the extracting by the component extraction unit and times at which the specific waveforms occur.

Advantageous Effects of Invention

The embodiment realizes an effect that, by extracting a requested component from multiple given waveforms that are cut out of multiple signal waveforms based on detected biological signals and, while referring to the display of the time of occurrence of the given waveforms, accepting selecting an extraction result as a noise component from multiple extraction results, it is possible, without any external device, to extract a noise signal from a complicated signal in which a signal to be acquired and the noise signal are mixed and enable confirmation that the noise removal process is optimum.

DESCRIPTION OF EMBODIMENTS

Figure 1:
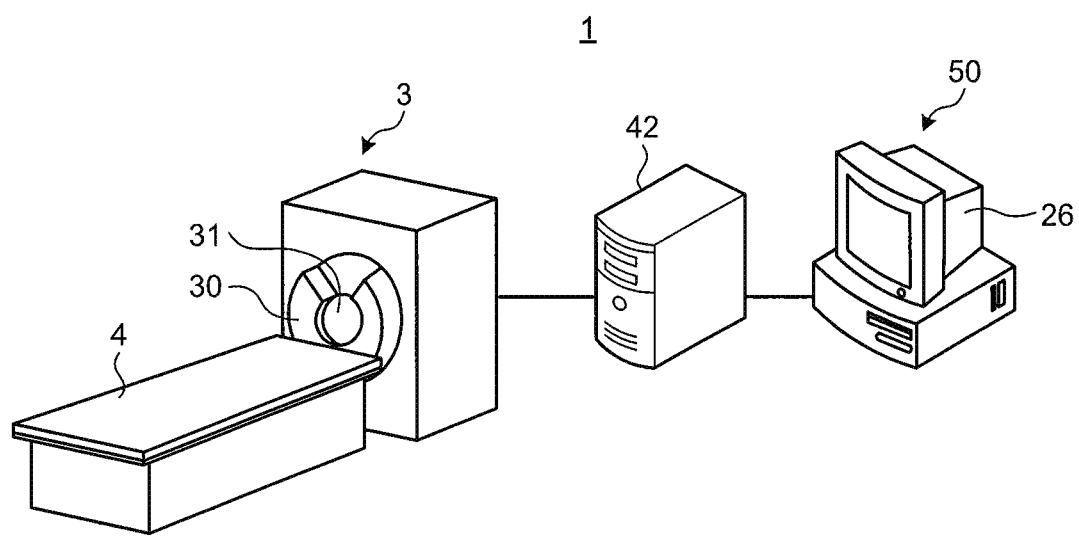
FIG. 1 is a schematic diagram of a biological signal measurement system according to an embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

FIG. 1 is a schematic diagram of a biological signal measurement system 1 according to an embodiment. The biological signal measurement system 1 measures and displays multiple types of biological signals, such as MEG (Magneto-encephalogram) signals and EEG (Electro-encephalogram) signals.

As illustrated in FIG. 1, the biological signal measurement system 1 includes a measurement device 3, a measurement table 4, a data recording server 42, and an information display device 50. The information display device 50 includes a monitor display 26 that displays signal information obtained by measurement and the result of analysis. In the embodiment, the data recording server 42 and the information display device 50 are provided separately; however, at least part of the data recording server 42 may be incorporated into the information display device 50.

A measurement subject on which measurement is performed lies supine on the measurement table 4 with his/her head attached with electrodes (or sensors) for MEG measurement and with the head put in a hollow 31 of a Dewar 30. The Dewar 30 is a container that maintains an ultralow-temperature environment with liquid helium and in which a large number of magnetic sensors for MEG measurement are arranged on the inner side the hollow 31 of the Dewar 30. The measurement device 3 collects MEG signals from the electrodes and EEG signals from the magnetic sensors. The measurement device 3 outputs the collected biological signals to the data recording server 42.

In general, the Dewar 30 incorporating the magnetic sensors and the measurement table 4 are arranged in a magnetic shielding room; however, the magnetic shielding room is omitted for convenience of illustration in the drawing.

The data recording server 42 records data, such as the biological signals that are output from the measurement device 3.

The information display device 50 reads the data that is recorded in the data recording server 42, displays the data on the monitor display 26, and analyzes the data. The information display device 50 displays waveforms of the MEG signals from the multiple magnetic sensors and the waveforms of the EEG signals from the multiple electrodes on the same time axis in synchronization with each other. The EEG signals represent the electric activities of nerve cells (the flow of ion charges occurring at dendrites of neurons in synaptic transmission) as voltage values between electrodes. The MEG signals represent minute variations of the magnetic fields generated by the electric activities of the brain. Brain magnetic fields are sensed by a highly sensitive superconducting quantum interference device (SQUID) sensor.

Figure 2:
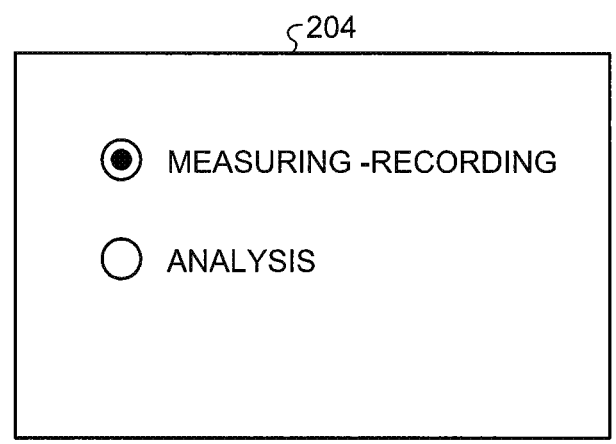
FIG. 2 is a front view illustrating an exemplary start screen.

FIG. 2 is a front view illustrating an exemplary start screen 204 that is displayed on the monitor display 26 of the information display device 50. As illustrated in FIG. 2, "measuring-recording" and "analysis" choice boxes are displayed on the start screen 204 that is displayed on the monitor display 26 of the information display device 50. In the case of EEG and/or MEG measurement, measuring and recording data and analyzing data are often performed by different units. For example, when the "measuring-recording" box on the start screen 204 is chosen by a measurement technologist (measurer), the measurement device 3 saves the measured data in the data recording server 42 sequentially. The information display device 50 reads the data saved in the data recording server 42 and displays the data on the monitor display 26. After the measuring and recording, when the "analysis" choice box on the start screen 204 is chosen by an analyzer, such as a doctor, the information display device 50 reads the measurement data saved in the data recording server 42 and analyzes the measurement data.

Operations on Measuring and Recording

First of all, operations performed by the information display device 50 on measuring and recording will be described.

Figure 3:
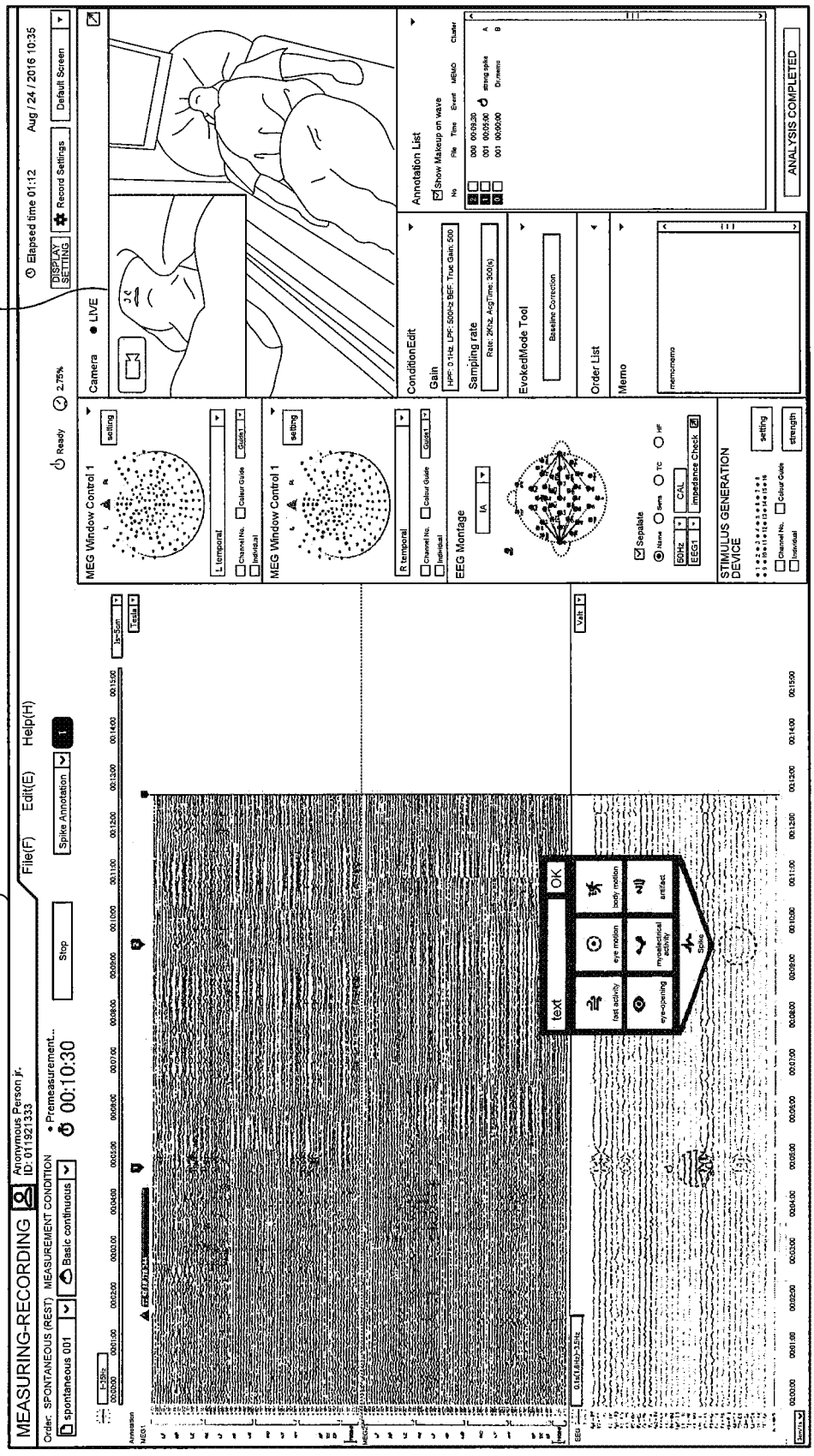
FIG. 3 is a front view illustrating an exemplary measuring-recording screen.

FIG. 3 is a front view illustrating an exemplary measuring-recording screen 205 that is displayed on the monitor display 26 of the information display device 50 on measuring and recording. As illustrated in FIG. 3, the measuring-recording screen 205 displays that that this is a "measuring-recording" screen on a tab 111. The measuring-recording screen 205 includes an area 201A to display measured signal waveforms and an area 201B to display monitor information other than the signal waveforms. The area 201A to display signal waveforms are arranged on the left in the screen when viewed from the measurer and the area 201B to display monitor information other than signal waveforms is arranged on the right in the screen when viewed from the measurer. The measuring-recording screen 205 does not cause any extra shift in the measure's view in accordance with the move of the waveforms that are detected and displayed in real time (displayed from the left side to the right side on the screen) and any extra shift in moving the mouse from the area 201A on the left in the screen to the area 201B on the right in the screen, which improves operation efficiency.

The measuring-recording screen 205 displays a monitor window 170 for checking the state of the measurement subject during measurement on the area 201B of the display screen. The measuring-recording screen 205 displays live images of the measurement during measurement and thus, as described below, is able to enhance reliability of checking signal waveforms and determination.

The measuring-recording screen 205 illustrated in FIG. 3 represents the case where the whole measuring-recording screen 205 is displayed on the display screen of the single monitor display 26. The area 201A on the left and the area 201B on the right may be displayed independently on two or more monitor displays separately.

Figure 4:
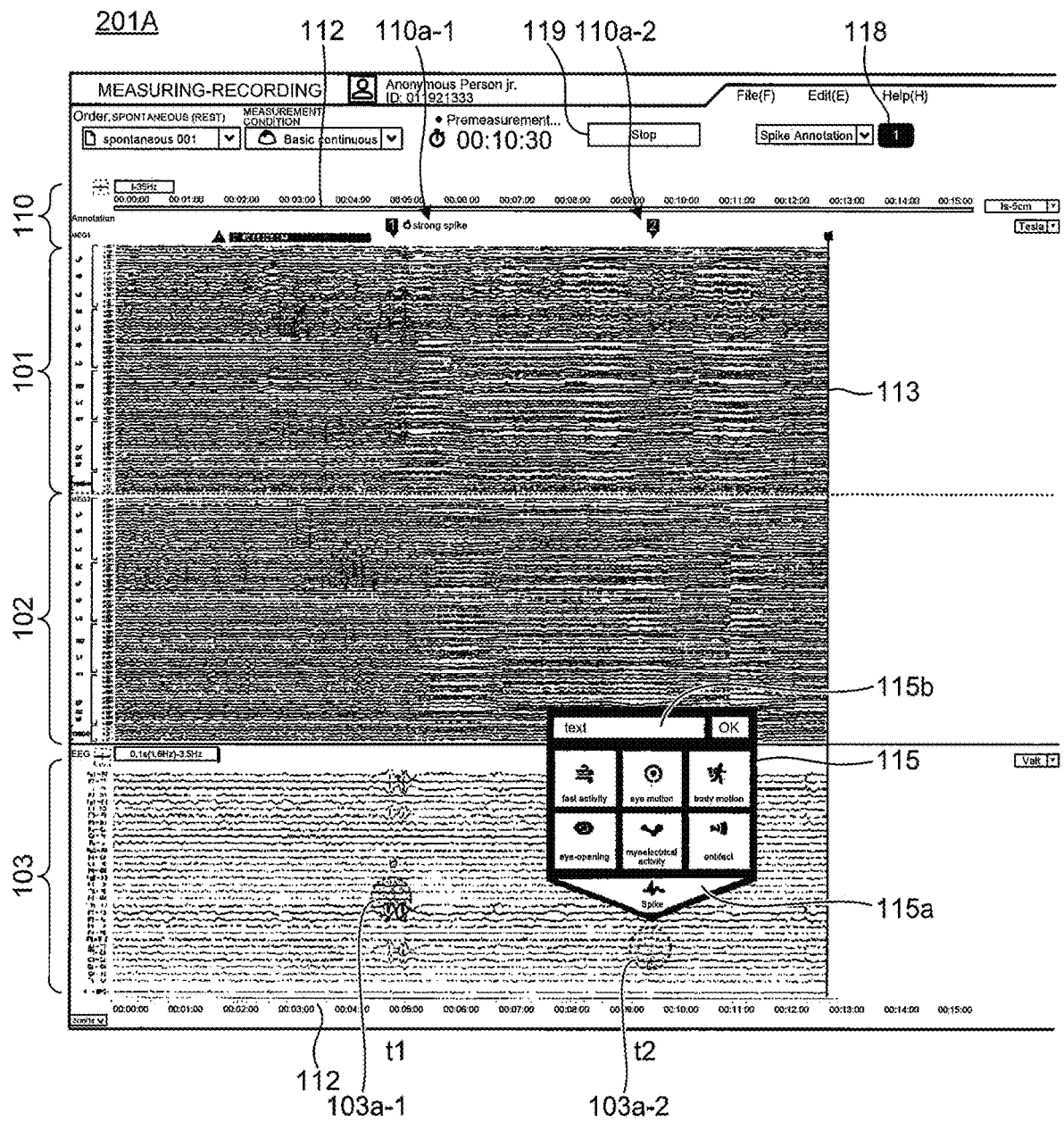
FIG. 4 is an enlarged view of an area on the left in the measuring-recording screen.

FIG. 4 is an enlarged view of the area 201A on the left in the measuring-recording screen 205. As illustrated in FIG. 4, the area 201A includes a first display part 110 to display signal detection time information in a horizontal direction of the screen (in a first direction) and second display parts 101 to 103 to display multiple signal waveforms based on the signal detection the vertical direction of the screen (in a second direction).

The time information displayed on the display part 110 is, in the example in FIG. 4, a timeline containing time displays added along a time axis 112. Only the band-like axis may be displayed without display of the times (numbers) or only the times (numbers) may be displayed without provision of the axis. The time axis 112 may be displayed on the lower side of the display part 103 in addition to the upper side of the screen to display the timeline.

In the area 201A of the measuring-recording screen 205, multiple signal waveforms that are acquired from the same type of multiple sensors or multiple types of signal waveforms that are acquired from multiple types of sensor groups are displayed in synchronization with one another along the same time axis. For example, the waveforms of multiple MEG signals that are obtained from the right side of the head of the measurement subject are displayed in parallel on the display part 101 and the waveforms of multiple MEG signals that are obtained from the left side of the head of the measurement subject are displayed in parallel on the display part 102. On the display part 103, the waveforms of multiple MEG signals are displayed in parallel. The multiple EEG signal waveforms are voltage signals that are measured between each electrode. Each of the multiple signal waveforms is displayed in association with the identification number of the sensor by which the signal is acquired or in association with the channel number.

When measurement is started and measurement information from each sensor is collected, the information display device 50 displays signal waveforms from the left end of each of the display parts 101 to 103 of the area 201A in the right direction over time. A line 113 of the measuring-recording screen 205 represents the time (present) and moves from the left to the right in the area 201A. When the signal waveforms are displayed to the right end of the area 201A (the right end of the time axis 112), the information display device 50 deletes the signal waveforms gradually from the left end of the screen to the right, displays new signal waveforms in the position of the deletion sequentially from the left in the right direction and moves the line 113 from the left end to the right. The information display device 50 displays the elapse of time on the time axis 112 in accordance with the progress of the measurement in the horizontal display part 110. The measuring and recording in the data recording server 42 is continued until an end button 119 is pressed.

When the measurer (the recorder) notices a noise waveform, waveform unsteadiness or an amplitude singularity on the signal waveforms while recording data, the information display device 50 accepts marking on the signal waveforms corresponding to the problematic spot or area on the area 201A of the measuring-recording screen 205. It is possible to specify the spot or area to be marked by a pointer operation or a click operation with a mouse. The information display device 50 displays the specified spot (or area) in an enhanced manner on the signal waveforms in the display parts 101 to 103 and makes a display along the time axis 112 in the display part 110 in a time position or a time range that the specifying result corresponds. The information display device 50 saves the information about the marking containing the display on the time axis 112 together with the signal waveform data. The spot specified in the area 201A of the measuring-recording screen 205 corresponds to a time and the area specified in the area 201A of the measuring-recording screen 205 correspond to a certain area containing the time.

In the area 201A of the measuring-recording screen 205 exemplified in FIG. 4, an area containing one or more channels in the display part 103 is specified at a time t1 and a time containing the time t1 is displayed in a highlighted manner with a mark 103a-1. In the area 201A of the measuring-recording screen 205 exemplified in FIG. 4, an annotation 110a-1 representing the specifying result is displayed in a corresponding time position in the display part 110 in connection with the display of the mark 103a-1. Furthermore, in the area 201A of the measuring-recording screen 205 exemplified in FIG. 4, another waveform position and the vicinity of the waveform position is marked in the display part 103 at a time t2 and a mark 103a-2 is displayed in a highlighted manner in the position (a time t2) or an area in the vicinity of the position (at least any one of a time range of multiple waveforms is specified). At the same time, in the area 201A of the measuring-recording screen 205 exemplified in FIG. 4, an annotation 110a-2 is displayed in a corresponding time position (time range) in the display part 110.

The annotation 110a-1 added to the display part 110 at the time t1 contains, for example, an annotation identification number and information representing the attribute of the waveform. In this example, together with an annotation number "1", an icon representing the waveform attribute and text information "strong spike" are displayed.

As illustrated in FIG. 4, when the measurer specifies another waveform spot or an area in the vicinity of the spot at the time t2, the information display device 50 displays the mark 103a-2 in a highlighted manner in the specified spot and displays an annotation number "2" in a corresponding time position in the display part 110. Furthermore, the information display device 50 displays a pop-up window 115 for selecting an attribute in the spot displayed in a highlighted manner. The pop-up window 115 includes selection buttons 115a to select various attributes and an input box 115b to input a comment or additional information. On the selection buttons 115a, causes of waveform unsteadiness, such as "fast activity", "eye motion", "body motion" and "spike", are represented as the waveform attributes. As the measurer is able to check the state of the measurement subject on the monitor window 170 in the area 201B of the screen, the observer is able to properly select the attribute representing the cause of the waveform unsteadiness. For example, when a spike occurs in a waveform, it is possible to determine whether the spike is one representing the symptom of epilepsy or one resulting from a body motion (such as sneeze) of the measurement subject.

The same operation is performed at the time t1 and, according to FIG. 4, the selection button 115a of "spike" is selected on the pop-up window 115 and "strong spike" is entered in the input box 115b and thus the annotation 110a-1 is displayed in the display part 110. Such a display mode makes it possible to, when a large number of signal waveforms are displayed in synchronization with one another on the same time axis 112, easily specify a spot or area of interest in the signal waveforms by checking by sight and easily grasp basic information of the spot of interest.

Note that part of or all the annotation 110a-1, for example, at least one of the attribute icon and the text annotation, may be displayed in the vicinity of the mark 103a-1 on the signal waveforms in the display part 103. As adding an annotation onto the signal waveforms may hinder checking the waveform shapes, it is desirable that, when an annotation is displayed on the signal waveforms in the display parts 101 to 103, it is possible to choose displaying or not displaying the annotation.

The area 201A of the measuring-recording screen 205 includes a counter box 118. The counter box 118 displays the cumulative total of spike annotations. Every time "spike" is selected, the information display device 50 increments the counter value of the counter box 118 to make it possible to see the total of spikes from the start of recording until now (the line 113) at one sight.

Figure 5:
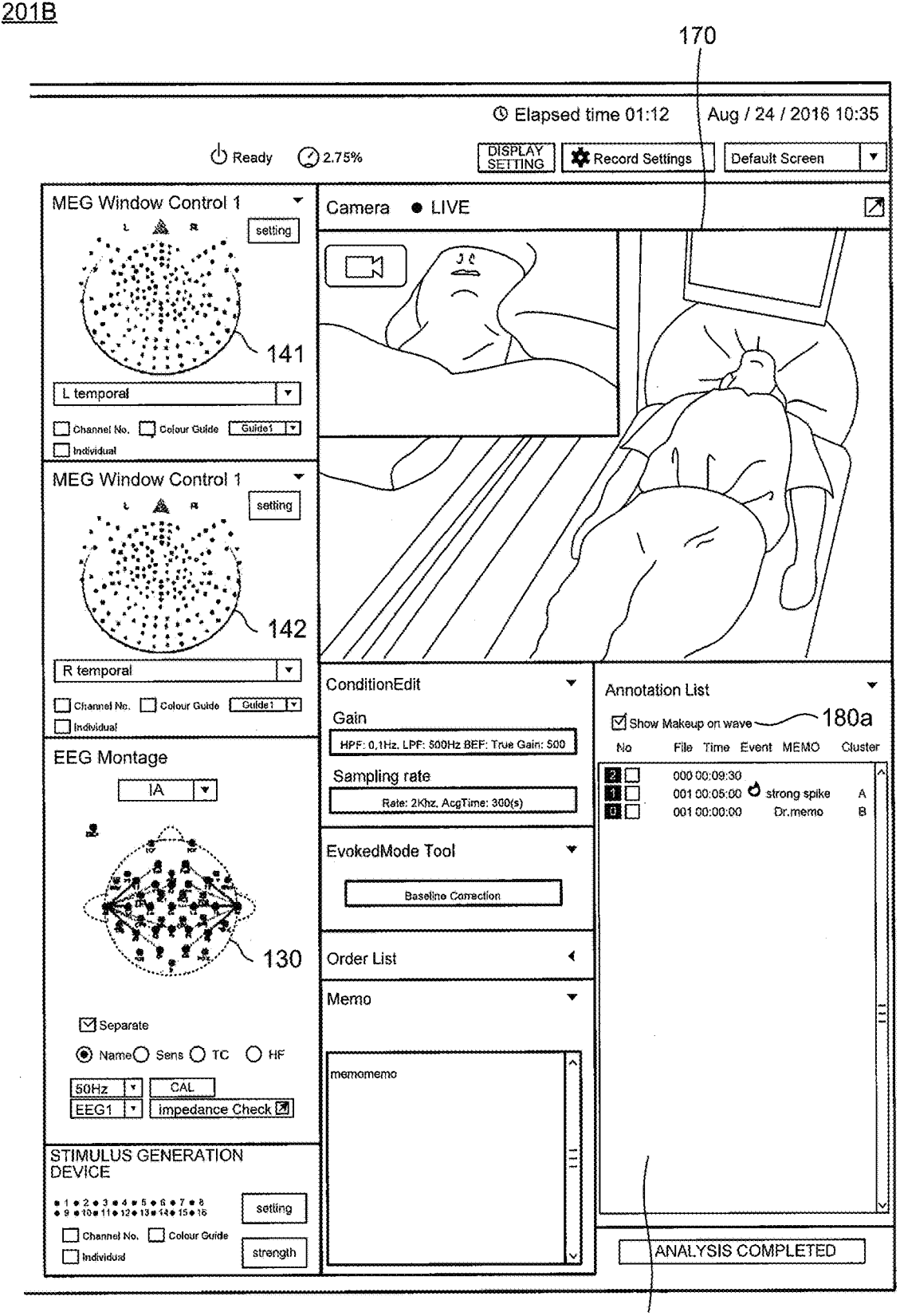
FIG. 5 is an enlarged view of an area on the right in the measuring-recording screen.

FIG. 5 is an enlarged view of the area 201B on the right in the measuring-recording screen 205 and illustrates the state at the same time as that according to FIG. 4 (the time point on the line 113). The information display device 50 displays live images of the state of the measurement subject lying on the measurement table 4 with the head in the measurement device 3 on the monitor window 170 of the area 201B of the measuring-recording screen 205. The information display device 50 displays distribution maps 141, 142 and 130 that correspond respectively to the sets of signal waveforms in the display parts 101, 102 and 103 and an annotation list 180 in the area 201B of the measuring-recording screen 205.

The annotation list 180 is a list of annotations of the marks on the signal waveforms in FIG. 4. Every time a position or an area on the signal waveforms is specified in the display parts 101 to 103 and an annotation is added, corresponding information is added sequentially to the annotation list 180. The addition to and display of the annotation list 180 on the measuring-recording screen 205 is performed, for example, in the descending order (new data is displayed on the top); however, the order is not limited this example. The display of the annotation list 180 may be performed in the ascending order, but note that the correspondence relationship with the annotations displayed along the time axis 112 in the display part 110 is seeable. Furthermore, it is also possible to change the display order or perform sorting according to each item.

In the exemplary annotation list 180 illustrated in FIG. 5, the time information corresponding to the annotation number "1" and the added annotation information are listed. An attribute icon representing "spike" and texts "strong spike" are recorded as the annotation information. In the exemplary annotation list 180 illustrated in FIG. 5, the time information corresponding to the annotation number "2" is listed at the time when the mark 103a-1 is displayed in a highlighted manner.

The information display device 50 arranges the display/non-display choice box 180a to choose whether to display or not to display the annotation near the annotation list 180 in the area 201B of the measuring-recording screen 205. When not displaying is chosen on the choice box 180a, the annotations other than the highlighted mark on the signal waveforms are not displayed on the display parts 101 to 103 but the display of the annotations along the time axis 112 in the display part 110 is maintained. This makes the annotation information recognizable without hindering visibility of the signal waveforms.

Figure 6:
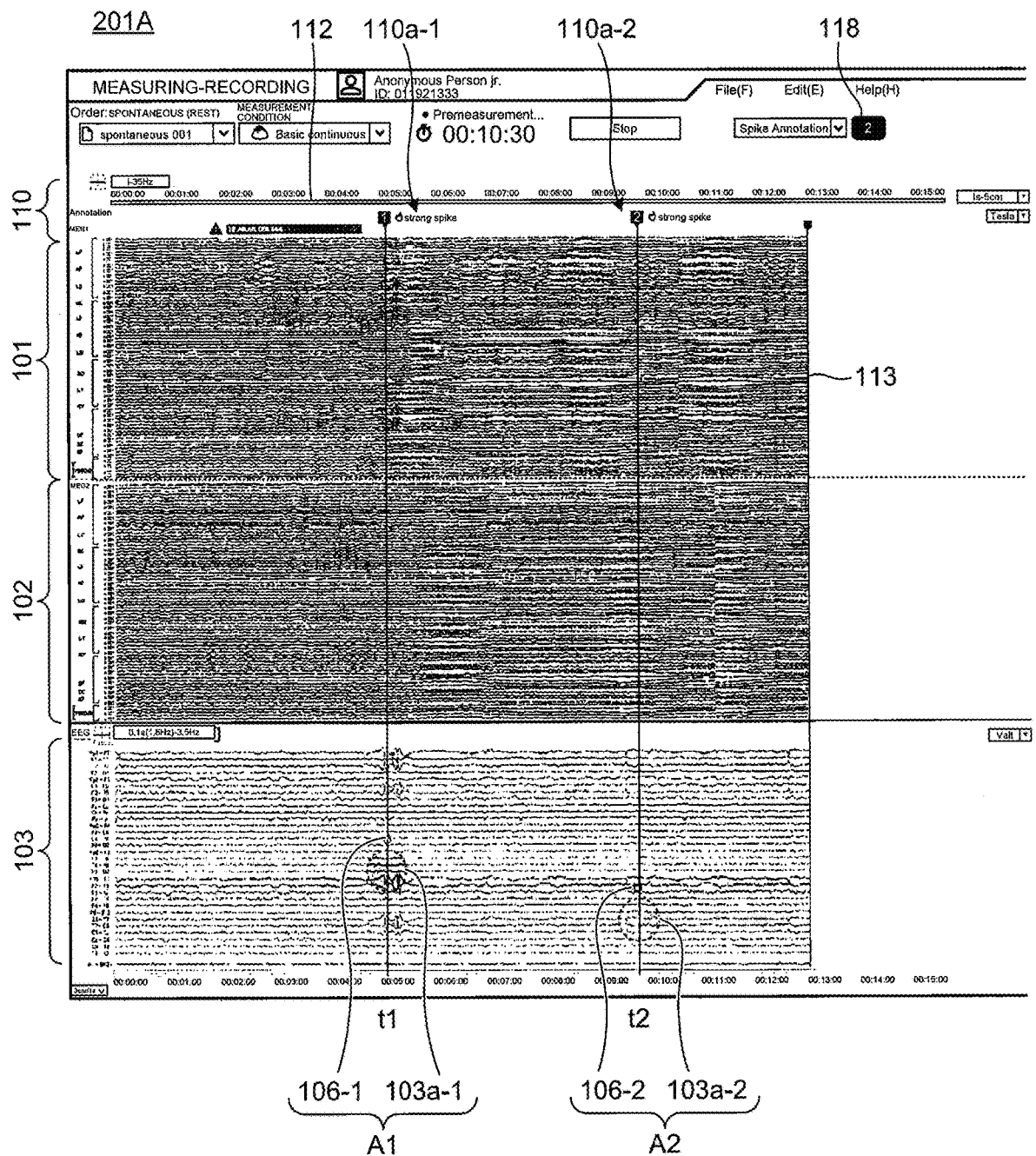
FIG. 6 is an enlarged view of the area on the left in the measuring-recording screen.

FIG. 6 is an enlarged view of the area 201A on the left in the measuring-recording screen 205 right after the selection of "spike" on the pop-up window 115 at the time t2 and the input of texts "normal spike". Once the "OK" button is chosen on the pop-up window 115 exemplified in FIG. 4, the information display device 50 closes the pop-up window 115 and displays the annotation 110a-2 in a corresponding time position in the display part 110 as illustrated in FIG. 6. The information display device 50 displays the attribute icon representing "spike" and text information "normal spike" in association with the annotation number "2". At the same time, the information display device 50 increments the value of the counter box 118. The information display device 50 further displays an attribute icon 106-2 in the vicinity of the mark 103a-2 displayed in a highlighted manner. In the example illustrated in FIG. 6, an attribute icon 106-1 is displayed in the vicinity of the mark 103a-1 and, as described above, it is possible to choose whether to display or not to display the attribute icons 106-1 and 106-1. An annotation A1 containing the mark 103a-1 and the attribute icon 106-1 and an annotation A2 containing the mark 103a-2 and the attribute icon 106-2 are contained in the annotation information.

Figure 7:
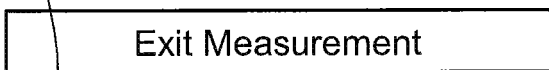
FIG. 7 is an enlarged view of an annotation list.

FIG. 7 is an enlarged view illustrating the annotation list 180. In response to the addition of the annotation corresponding to the mark 103a-2 to the area 201A on the left in the screen, the information display device 50 updates the annotation list 180. As illustrated in FIG. 7, a memo "normal spike" is added to the annotation number "2" in the annotation list 180.

Thereafter, in the same manner, every time a given spot or area on the signal waveforms is specified in the area 201A during the measuring, the specified spot is displayed in an enhanced manner and annotation information is displayed along the time axis 112 in the display part 110. In the area 201B, annotation information is added sequentially to the annotation list 180.

In the annotation list 180 and the area 201A on which the signal waveforms are displayed, displaying annotation numbers is not essential and need not be used. Any information may be used as identification information as long as the information identifies the added annotation. For example, an attribute icon and an attribute character string (such as "strong spike") may be displayed in association with a time in the vicinity of the time axis 112. Furthermore, a file number (the number displayed in the item "File" in FIG. 6) may be displayed together in the area 201A.

Once the end button 119 (illustrated in FIG. 4) in the area 201A on the left in the measuring-recording screen 205 is chosen (pressed) and the measurement ends, the information display device 50 saves the highlighted spots that are specified in the display parts 101 to 103 in association with the signal waveforms. The information display device 50 also saves the annotation information displayed in the corresponding time positions in the display unit 110 in association with the annotation numbers and the times. The information display device 50 also saves relative information, such as the counter value of the counter box 118 and the content of the annotation list 180. The information display device 50 saves the display information and thus, even when the measurer and the analyzer are different from each other, the analyzer is able to recognize the problematic spot easily and analyze the spot.

Figure 8:
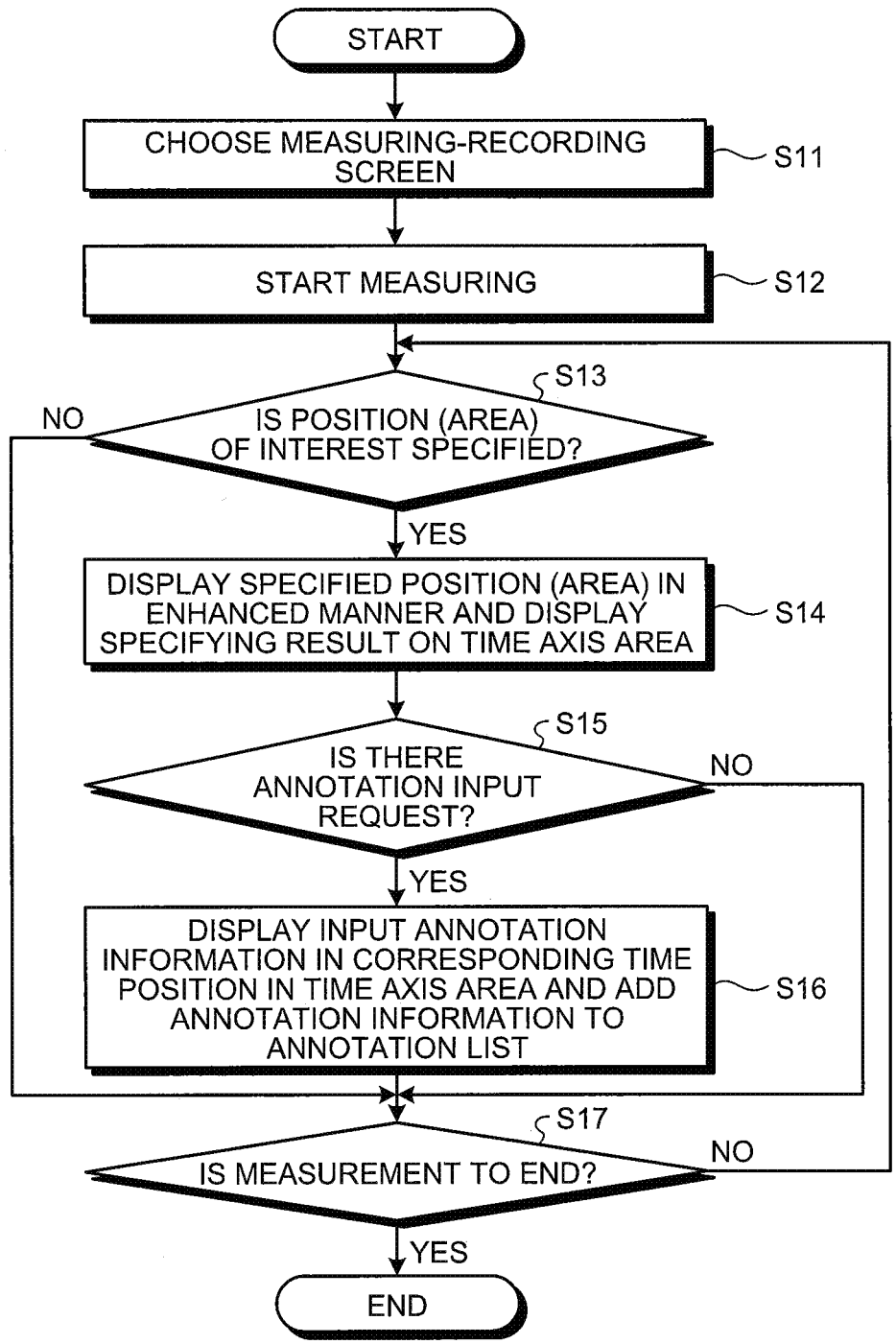
FIG. 8 is a flowchart schematically illustrating a flow of an information display process at the stage of measuring and recording.

FIG. 8 is a flowchart schematically illustrating the flow of the information display process at the stage of measuring and recording that is performed by the information display device 50.

As illustrated in FIG. 8, when "measuring-recording" is chosen on the start screen 204 illustrated in FIG. 2 (S11), the information display device 50 causes the measurement device 3 to start measuring and displays waveforms of multiple signals along the same time axis in synchronization with one another (S12). The "multiple signal waveforms" herein include signal waveforms that are detected by the same type of multiple sensors and signal waveforms that are detected by each of different types of sensors.

The information display device 50 determines whether a spot or area of interest is specified on the displayed signal waveforms (S13).

When a position or area of interest is specified (YES at S13), the information display device 50 displays the specified spot in an enhanced manner in a signal waveform display area (the display parts 101 to 103) and displays the result of the specifying on a corresponding time position in a time axis area (the display part 110) (S14). The specifying result contains information representing that the specifying is performed or information identifying the specifying.

Along with, before or after the display of the specifying result in the time axis area, the information display device 50 determines whether there is an annotation input request (S15).

When there is an annotation input request (YES at S15), the information display device 50 displays the input annotation information in the corresponding time position in the time axis area and adds the annotation information to the annotation list (S16).

The information display device 50 then determines whether a measurement end command is input (S17).

When no position (area) of interest is specified (NO at S13) and when there is no annotation input request (NO at S15), the information display device 50 skips to step S17 to determine whether to end the measurement. The information display device 50 repeats steps S13 to S16 until the measurement ends (YES at S17).

The information display method provides the measuring-recording screen 205 with high visibility of signal information when signals from multiple sensors are collected.

Operation to perform analysis

Operations performed by the information display device 50 on analyzing will be described.

Figure 9:
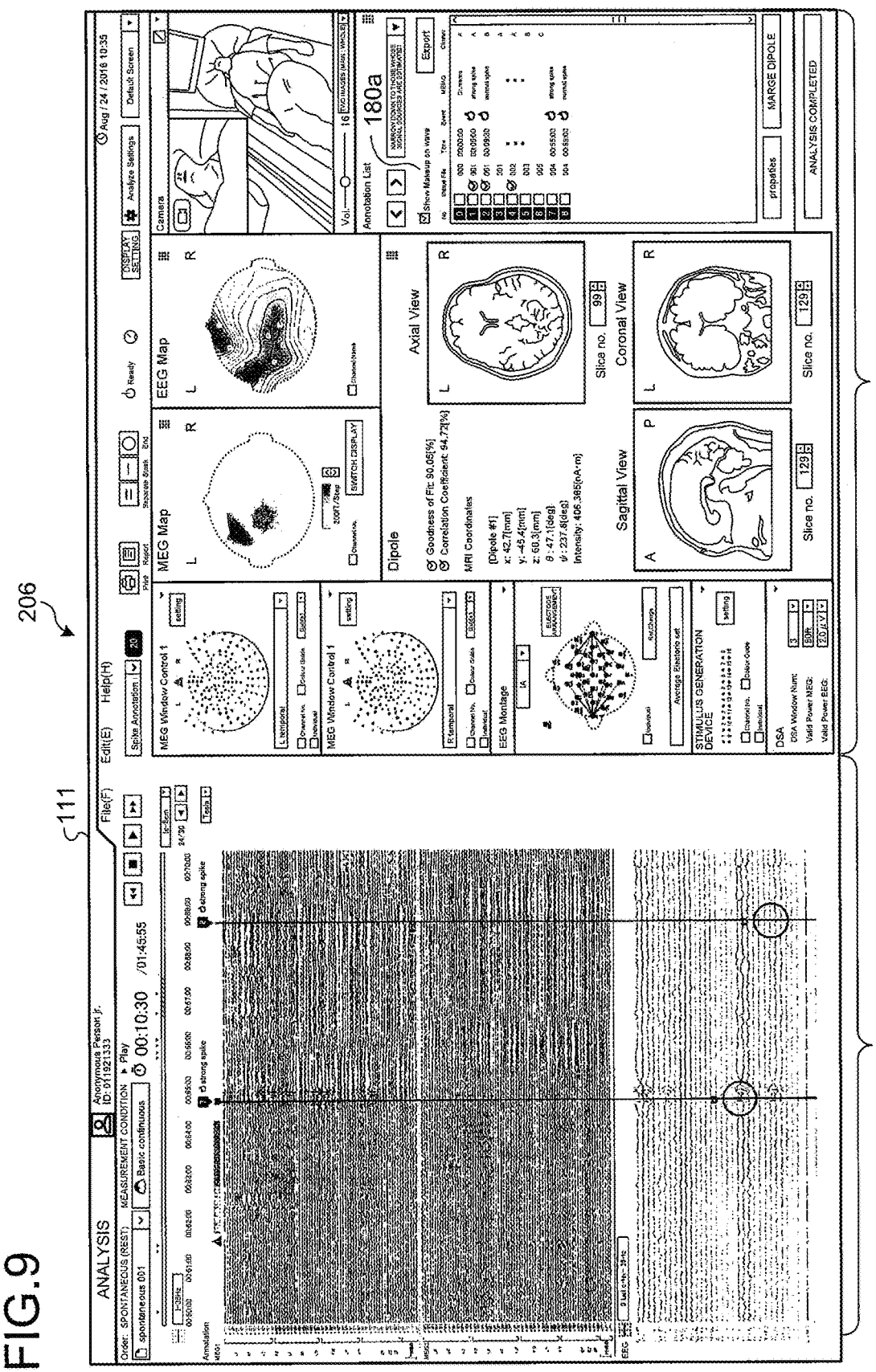
FIG. 9 is a front view illustrating an analysis screen.

FIG. 9 is a front view illustrating an exemplary analysis screen 206 that is displayed on the monitor display 26 of the information display device 50 on analyzing. As illustrated in FIG. 9, the analysis screen 206 is displayed by choosing the "analysis" button on the start screen in FIG. 2. The analysis screen 206 displays that this is an "analysis" screen on the tab 111. The analysis screen 206 includes an area 202A to display recorded signal waveforms together with annotations and an area 202B to display analysis information. The area 202A to display the recorded signal waveforms and the annotation information is arranged on the left in the screen when viewed from the measurer and the area 202B to display the analysis information is arranged on the right when viewed from the measurer because this increases, on analysis, the efficiency of an operation to operate a mouse or the like while checking the signal waveforms or selecting a signal waveform in the area 202A to check or determine the analysis result in the area 202B.

The analysis screen 206 displays the waveforms of the MEG signals in the second display parts 101 and 102 above the screen for the wave forms of the EEG signals in the second display part 103 of the area 202A. The analysis screen 206 displays the MEG distribution maps 141 and 142 in a screen area on a side close to the area 202A and on the upper side of the screen in the area 202B on the right of the area 202A and displays the EEG distribution map 130 under the MEG distribution maps 141 and 142. Thus, the analyzer is able to shift the view (in this case, clockwise) in the following order: from "the waveforms of EEG signals" in the second display part 103 to "the waveforms of MEG signals" in the second display parts 101 and 102, to the MEG distribution maps 141 and 142, and to the EEG distribution map 130. This makes the shift of the analyzer's (or observer's) view efficient and accordingly makes it possible to improve the analysis operation efficiency. The clockwise shift has been described above; however, the shift is not limited to this example.

Figure 10:
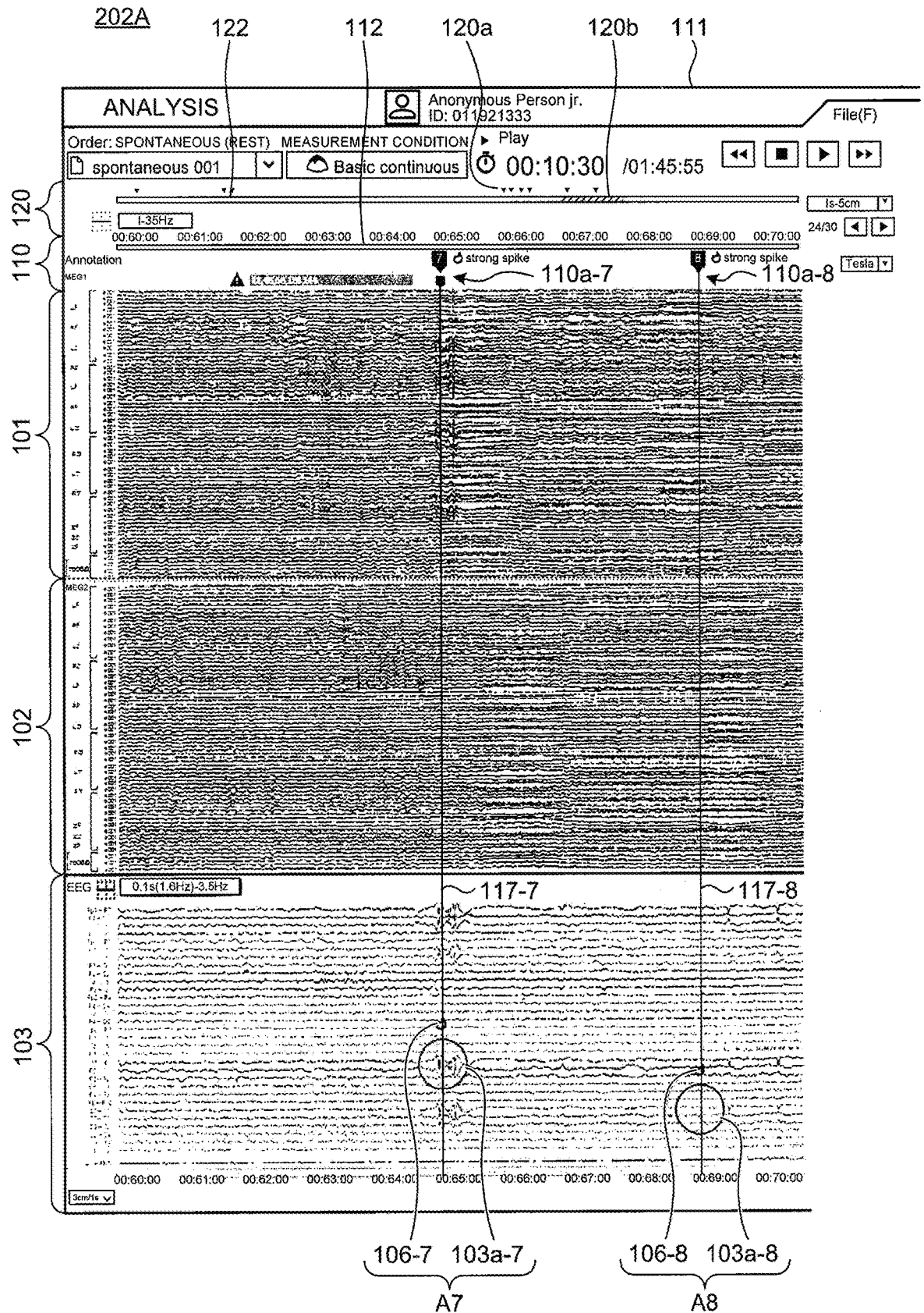
FIG. 10 is an enlarged view of an area on the left of the analysis screen.

FIG. 10 is an enlarged view of the area 202A on the left in the analysis screen 206. As illustrated in FIG. 10, the area 202A includes the display part 110 and a display part 120 to display time information on measuring is displayed in the horizontal direction of the screen (in the first direction) and the display parts 101 to 103 to display recorded signal waveforms in the vertical direction (in the second direction) according to each type.

The information display device 50 displays, on the display part 110, the time axis 112 representing the elapse of time on recording and annotations 110a-7 and 110a-8 that are added along the time axis 112. The information display device 50 displays a time axis 122 representing the entire recording time in the display part 120. The information display device 50 displays, along the time axis 122, pointer signs 120a each representing a time position in which an annotation is added and a time zone 120b representing the time band over which the signal waveforms currently displayed in the display parts 101 to 103 are recorded. The display enables the analyzer to intuitively grasp at which stage on measuring and recording the signal waveform currently analyzed is acquired.

After opening the analysis screen 206, the analyzer is able to display signal waveforms in a requested time band by dragging on the time zone 120b on the bar of the time axis 122. Alternatively, as describe below, by selecting a requested annotation from the annotation list 180, the analyzer is able to display the ante-posterior signal waveforms containing the annotation in the display parts 101 to 103.

In the area 202A of the analysis screen 206 exemplified in FIG. 10, annotations A7 and A8 that are added to the signal waveforms on recording are displayed in the display parts 101 to 103. In the area 202A of the analysis screen 206 exemplified in FIG. 10, marks 103a-7 and 103a-8 are displayed in a highlighted manner and corresponding attribute icons 106-7 and 106-8 are displayed in the vicinity of the marks 103a-7 and 103a-8. In the area 202A of the analysis screen 206 exemplified in FIG. 10, vertical lines 117-7 and 117-8 representing the time positions of the marks 103a-7 and 103a-8 are displayed. Displaying the line 117, for example, makes it possible to, when an annotation is added in connection with specifying a certain spot in the display part 103, easily check the result of the specifying by sight also in the display parts 102 and 101 that are different types of signal display areas. The line 117 may be contained in the annotation information as it makes it easy to check the annotation information by sight and thus may be referred to as an "annotation line". Selecting the line 117 enables enlarged display of the signal waveforms containing those in a certain ante-posterior period with respect to that time. This process will be described below.

Figure 11:
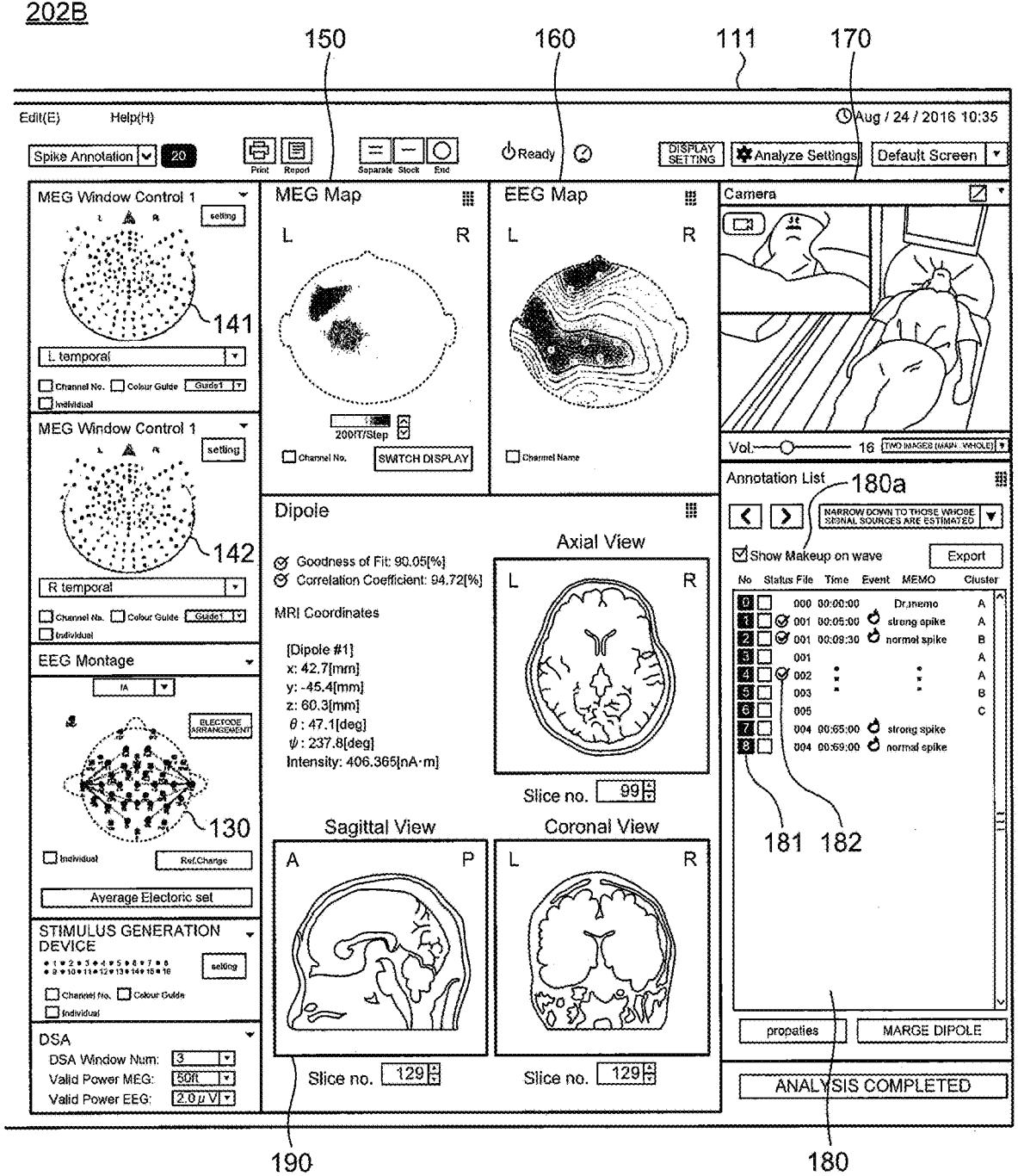
FIG. 11 is an enlarged view of an area on the right of the analysis screen.

FIG. 11 is an enlarged view of the area 202B on the right in the analysis screen 206 and illustrates the state at the same time as that in FIG. 10. The information display device 50 displays, in the area 202B of the analysis screen 206, the MEG distribution maps 141 and 142 corresponding to the signal waveforms that are displayed in the display parts 101 and 102 in the area 202A and the EEG distribution map 130 corresponding to the signal waveforms displayed in the display part 103 in the area 202A.

The information display device 50 displays, in the area 202B of the analysis screen 206, an MEG (Magneto-encephalogram) isofield contour map 150, a EEG (Electroencephalogram) map area 160, and a display window 190 of tomographic images of the brain of the measurement subject that are acquired by MRI (Magnetic Resonance Imaging). In the isofield contour map 150, the source area and the sink area are displayed in different colors and the directions of current flows are grasped by sight. The isofield contour map 150 and the map area 160 are information obtained after completion of the measurement and the MRI tomographic images are information obtained in a separate examination.

On the monitor window 170, video images of the measurement subject on measuring is displayed in synchronization with the time at which the signal waveforms in the display parts 101 to 103 in the area 202A are acquired. The analyzer is able to analyze the signal waveforms while watching the monitor window 170 to check the state of the measurement subject.

In the annotation list 180, all annotations that are added in the measuring and recording are listed. In the annotation list 180, annotation information (such as an attribute icon and text input information) added in association with an annotation number 181 is written. The annotation list 180 on the analysis screen 206 is displayed, for example, in the ascending order (such that old data is on the top); however, the display is not limited thereto. As in the case of the measuring-recording screen 205, using annotation numbers is not essential and an annotation may be identified according to the combination of, for example, the time, the file name and the attribute. The order in which the annotations contained in the annotation list 180 are displayed may be changed and may be sorted according to each item. Clicking the annotation number 181 or a row that is requested makes it possible to display, on the display parts 101 to 103 in the area 202A in FIG. 10, signal waveforms over a certain time band containing the time positon at which the annotation is added.

Not as in the case the measuring-recording screen 205, in the analysis screen 206, the information display device 50 displays estimation completion signs 182 (represented in FIG. 11) for annotations for which the analyzer checks the signal waveforms of the annotation part and estimates the signal source eventually.

The information display device 50 arranges the display/non-display choice box 180a to choose displaying or not-displaying the annotation near the annotation list 180 in the area 202B of the analysis screen 206. When not-displaying is specified on the choice box 180a, the attributed icons 106-7 and 160-8 disappear. Not displaying the highlighted marks 103a-7 and 103a-8 may be chosen on the display/non-display choice box 180a.

Figure 12:
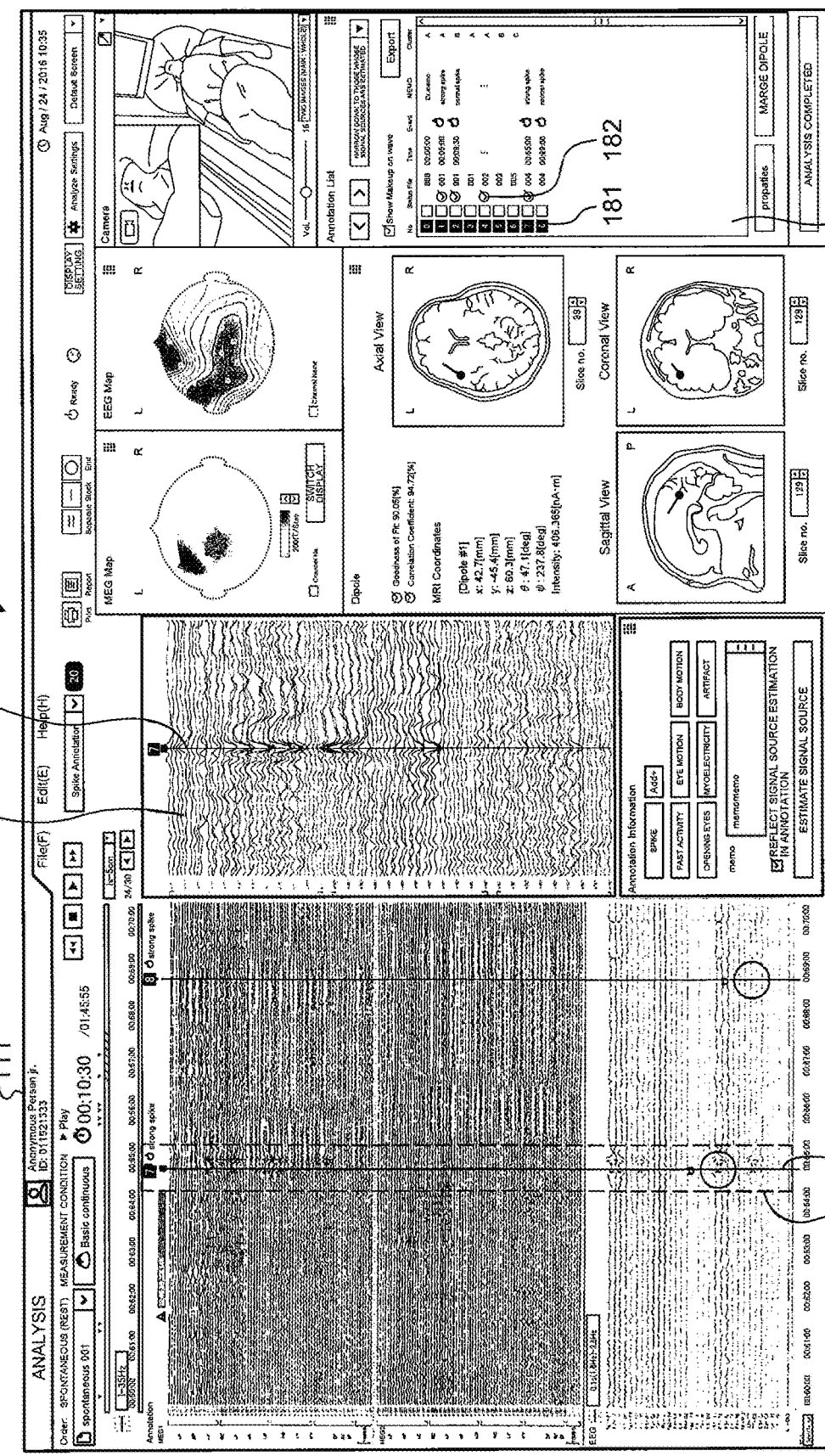
FIG. 12 is a front view of the analysis screen right after selection of a line.

FIG. 12 is a front view of the analysis screen 206 right after the selection of the line 117-7 (for example, by double clicking). When the analyzer focuses on the annotation A7 and selects the line 117-7 (for example, by double clicking) in order to analyze the waveforms of the area, the information display device 50 displays the signal waveforms in the highlighted signal waveform and the vicinity of the highlighted signal waveforms in an enlarged manner in an enlarged display part 200. The information display device 50 displays the signal waveforms in an enlarged manner over a certain time range represented by an area 114 together with a line 217-7 representing a time position.

Figure 13:
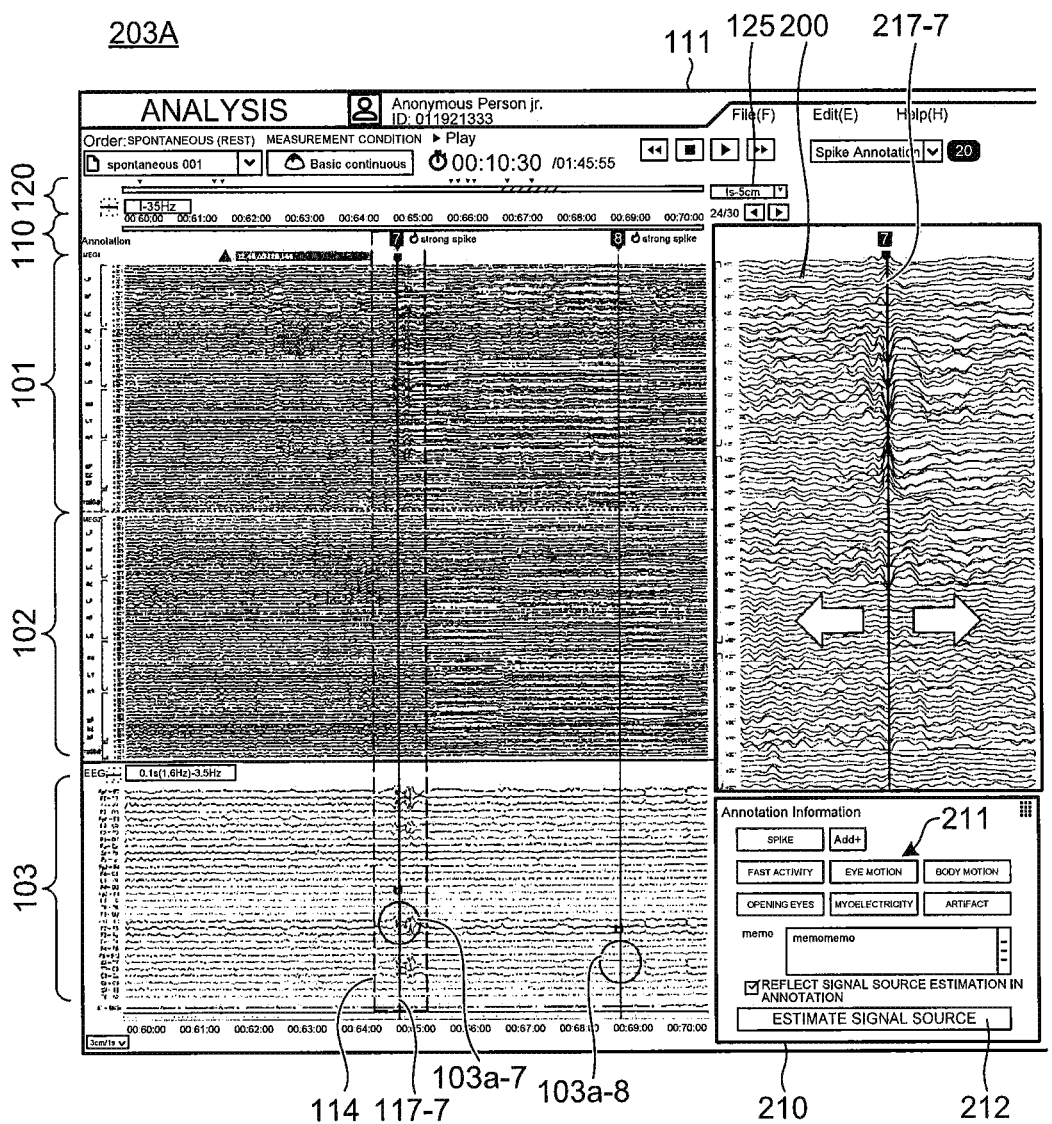
FIG. 13 is an enlarged view of an area on the left in the analysis screen illustrated in FIG. 12.

FIG. 13 is an enlarged view of an area 203A (a signal waveform display area) on the left in the analysis screen 206 illustrated in FIG. 12. Displaying the signal waveforms in an enlarged manner on the enlarged display part 200 as illustrated in FIG. 13 enables the analyzer to be able to re-check adequacy of the mark added on recording or check the waveform part that is not checked on measuring and recording. For example, the analyzer is able to specify or change the accurate spot of the problematic waveform by dragging the line 217-7 horizontally.

The information display device 50 may reflect the mark 103a that is displayed in a highlighted manner in the display part 103 and/or the attribute icon 106. Note that, as this may hinder checking by sight to determine an amplitude singularity, it is desirable that, when the highlighted mark 103a or the attribute icon 106 are displayed on the enlarged display part 200, it is possible to choose displaying or not displaying the highlighted mark 103a or the attribute icon 106.

The information display device 50 is also able to specify a type of signal waveforms to be displayed on the enlarged display part 200 and a channel range. For example, the analyzer shifts the view from the highlighted mark 103a-7 to the upper side of the screen and checks whether there is an amplitude singularity in the waveforms in the display parts 101 and 102 for MEG waveforms. In this case, by inputting a targeted channel area for the display part 101 or 102 in a box 125, it is possible to display the MEG waveforms relating to the mark 103a-7 in an enlarged manner in the enlarged display part 200.

As illustrated in FIG. 13, the information display device 50 displays a confirmation window 210 on the lower side of the screen of the enlarged display part 200. The confirmation window 210 contains signal wave attribute buttons 211 and a signal source estimation button 212. The signal wave attribute button 211 corresponds to the attribute information contained in the pop-up window 115 of the measuring-recording screen 205 and, when the attribute added on recording is erroneous, it is possible to select the attribute button 211 to select a correct attribute. When the selection of a correct signal waveform position and/or attribute is confirmed, the analyzer is able to reflect the estimation of the signal source in the annotation by clicking the signal source estimation button 212.

Figure 14:
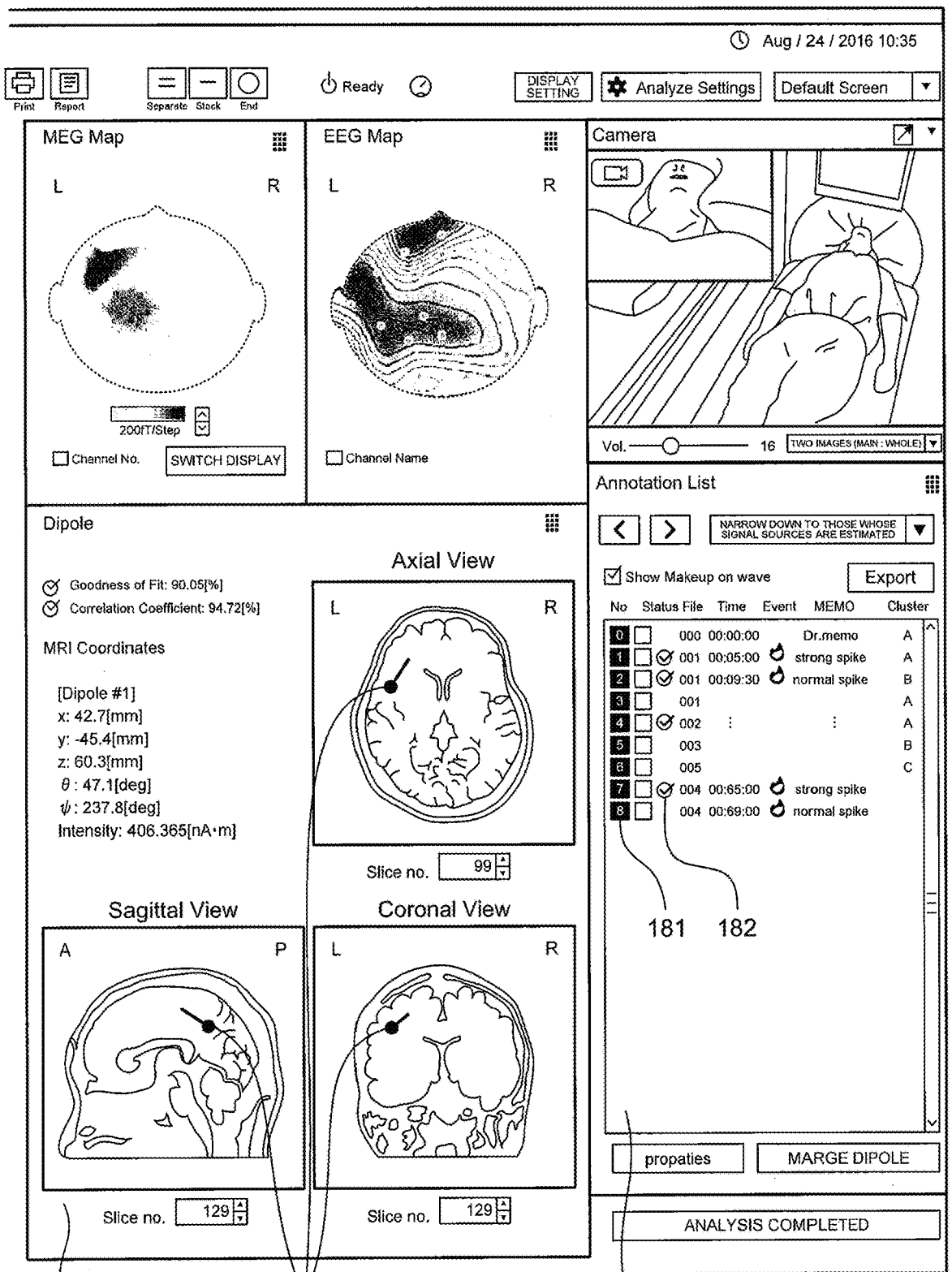
FIG. 14 is an enlarged view of an area on the right in the analysis screen illustrated in FIG. 12.

FIG. 14 is an enlarged view of the area 203B on the right in the analysis screen 206 illustrated in FIG. 12. When the signal waveform position and/or attribute is confirmed with respect to the requested annotation and the signal source estimation button 212 is selected, as illustrated in FIG. 14, the information display device 50 adds the estimation completion sign 182 to the corresponding annotation (in this example, the annotation number "7") in the annotation list 180. Furthermore, the information display device 50 displays a dipole estimation result 190a on the MRI tomographic images on the display window 190.

There are two types of methods of updating the annotation list 180 when the mark positions displayed in a highlighted manner in the display parts 101 to 103 and/or the content of the annotation 110a is changed. The methods include a method of reflecting only the latest information updated by the analyzer in the annotation list 180 and a method of adding the latest updated information as new annotation information while maintaining the annotation information on measuring and recording. When the latter method is employed, for example, a branch number from the annotation number on recording may be added as annotation identification information. In this case, new annotation information may be added to the display part 110 and the added annotation information may be displayed in a different color along the time axis.

Figure 15:
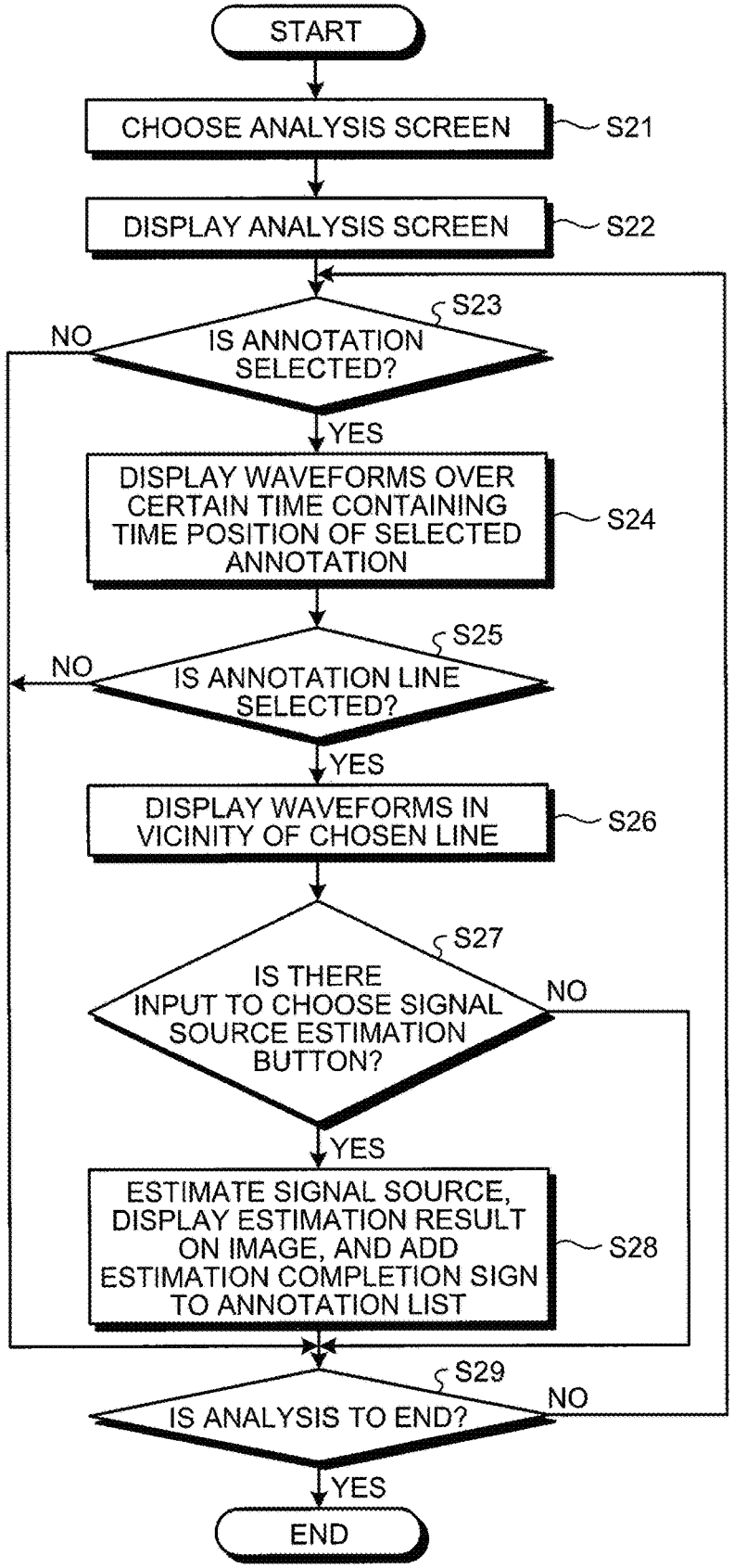
FIG. 15 is a flowchart schematically illustrating a flow of an information display process at the stage of analysis.

FIG. 15 is a flowchart schematically illustrating a flow of the information display process at the stage of analysis that is performed by the information display device 50.

As illustrated in FIG. 15, when "analysis" is chosen on the start screen 204 (see FIG. 2) (S21), the information display device 50 starts analysis and displays the analysis screen 206 (S22). The initial analysis screen 206 may be a blank screen on which no signal waveform is displayed or there may be of signal waveforms in a certain time range on the top or end of recording.

On displaying the analysis screen 206, the information display device 50 determines whether a given annotation is selected (S23). Selecting an annotation may be selecting a given annotation number or row in the annotation list 180 or specifying a time position by operating the time zone 120b on the time axis 122 in the display part 120.

Once an annotation is selected (Yes at S23), the information display device 50 displays signal waveforms over a certain time containing the time position of the selected annotation (S24).

The information display device 50 then determines whether the line 117 representing the time positon of a mark displayed in a highlighted manner is selected on the displayed scene (S25).

When the line 117 is selected (YES at S25), the information display device 50 displays the signal waveforms over the certain time range containing the selected line in an enlarged manner (S26). Enlarged display is not necessarily limited to signal waveforms in the vicinity of the mark that is displayed in a highlighted manner and different types of signal waveforms at the same time position may be displayed in an enlarged manner. For example, when a mark displayed in a highlighted manner is added to EEG signal waveforms, MEG signal waveforms at the same time position may be displayed in an enlarged manner. Furthermore, instead of displaying signal waveforms of all channels in an enlarged manner, signal waveforms acquired in a given range of channels containing the channel in which the marked signal waveforms are acquired may be displayed in an enlarged manner. In this case, whether there is an input to specify a type of signal waveforms to be displayed in an enlarged manner and/or a cannel range may be determined.

The information display device 50 determines whether the signal source estimation button 212 is pressed (S27).

When there is an input to choose the signal source estimation button 212 (YES at S27), the information display device 50 goes to S28 and performs computing to estimate a signal source. Specifically, the information display device 50 displays the estimation result on the MRI tomography screen and adds the estimation completion sign 182 to the annotation list 180 (S28).

The information display device 50 then determines whether an analysis end command is input (S29).

When no annotation is selected (NO at S23), no annotation line is selected for enlarged display (NO at S25) and no input is made to choose the signal source estimation button (NO at S27), the information display device 50 skips to step S29 and determines whether to end the analysis. The information display device 50 repeats steps S23 to S28 until an analysis end command is input (YES at S29).

The information display device 50 may determine whether the annotation is changed between steps S26 and S27. When the annotation is changed, the information display device 50 reflects the change in the annotation list 180 and moves to the determination at step S27.

The above-described display processing operations realize information display with excellent viewability and operability.

Figure 16:
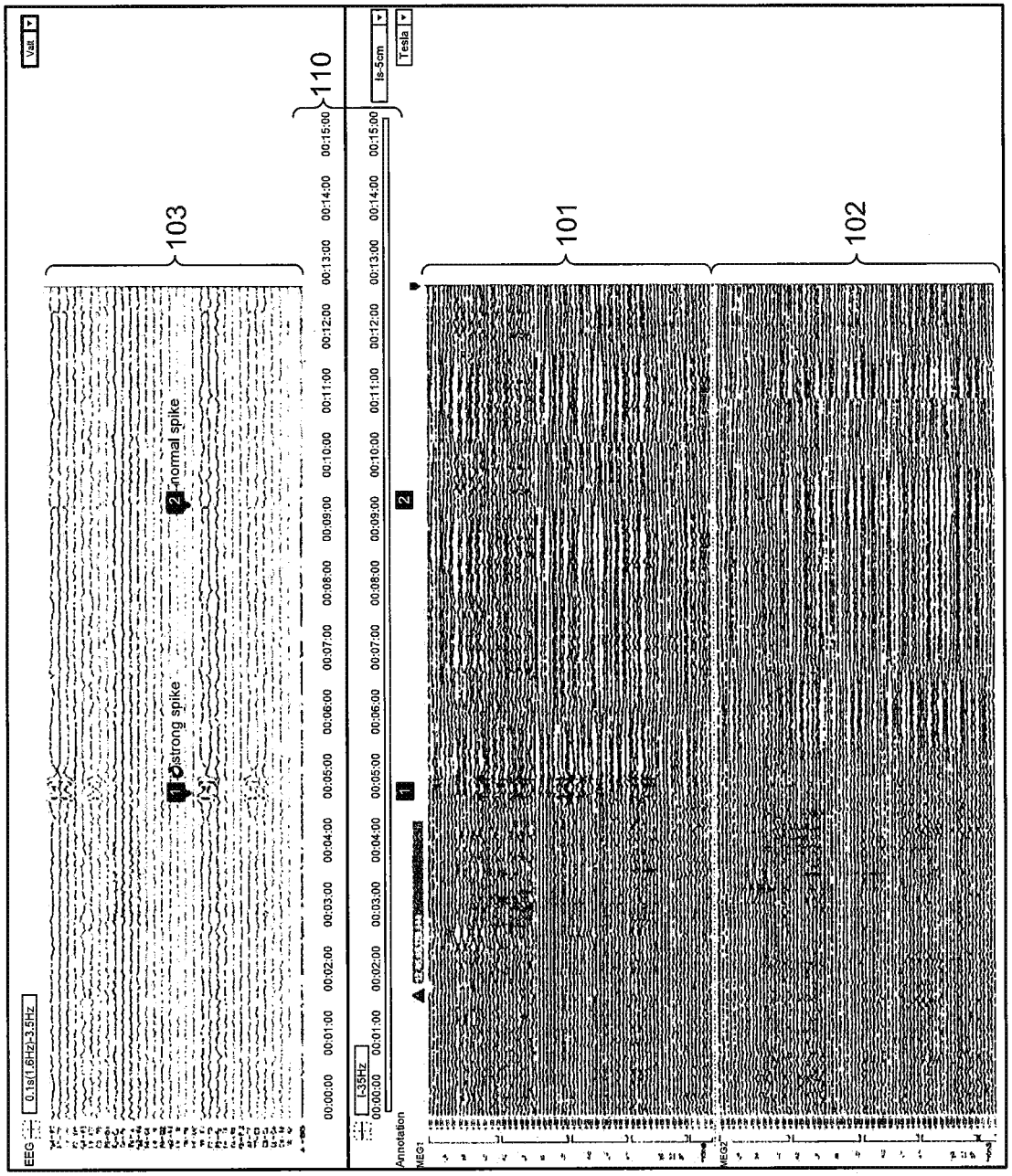
FIG. 16 is a diagram illustrating a modification of a display layout.
Figure 17:
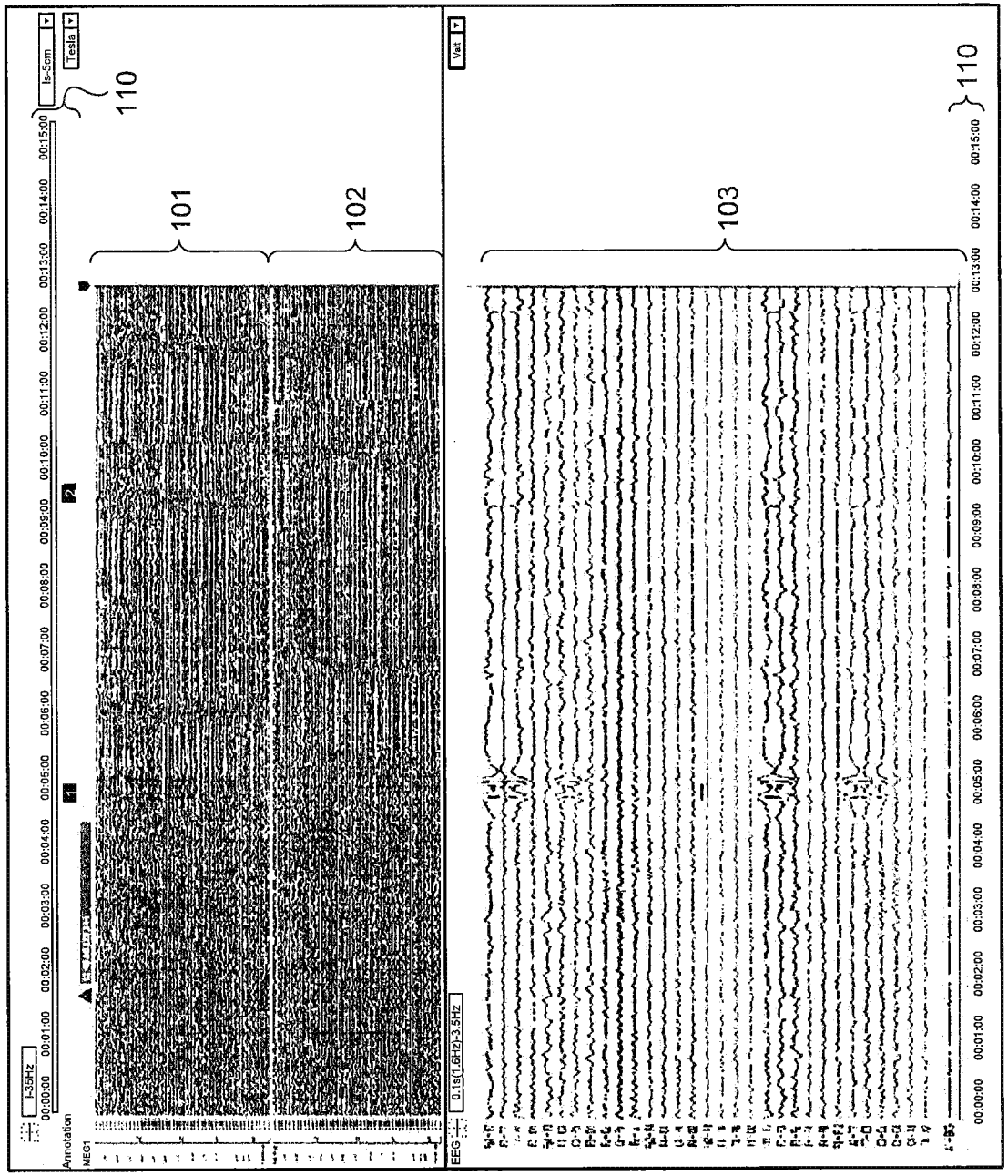
FIG. 17 is a diagram illustrating another modification of the display layout.

FIG. 16 and FIG. 17 are diagrams illustrating a modification of the display layout. When displaying signal waveforms from multiple types of sensors, the information display device 50 is able to set a display position properly according to the signal type.

For example, as illustrated in FIG. 16, the information display device 50 may arrange the display part 103 to display EEG signal waveforms whose amplitude is large and easy to view in the upper part of the screen. In this case, the MEG distribution maps 141 and 142 illustrated in FIG. 11 are arranged on the right of the display parts 101 and 102 and the EEG distribution map 130 is arranged on the right of the display part 103 and above the MEG distribution maps 141 and 142.

Furthermore, as illustrated in FIG. 17, the information display device 50 may change the vertical size of a given display part. For example, by choosing the frame of the display part 103 to display EEG waveforms and moving the screen vertically, it is possible to change the ratio between the vertical sizes of the display part 103 and the display parts 101 and 102.

Furthermore, without limiting the position of the display part 110 to display the timeline to the top end and bottom end of the screen, the information display device 50 may provide the display unit 110 between the MEG waveforms and the EEG waveforms. The information display device 50 may combine, for example, the timeline extending horizontally between the MEG waveforms and the EEG waveforms and a timeline arranged on the top end and/or the bottom end of the screen.

Noise Removal Process

A noise removal process to remove living-body dependent noises, such as magnetic fields generated by the heart and mixed in measured MEG signals. In the embodiment, the noise removal process on analysis will be described; however, the process is not limited thereto and executing the process on measuring and recording has no problem. The living-body dependent noises are not limited to magnetic fields generated by the heart (cardiac magnetic field noises) and, for example, include magnetic fields caused by twinkling.

Figure 18:
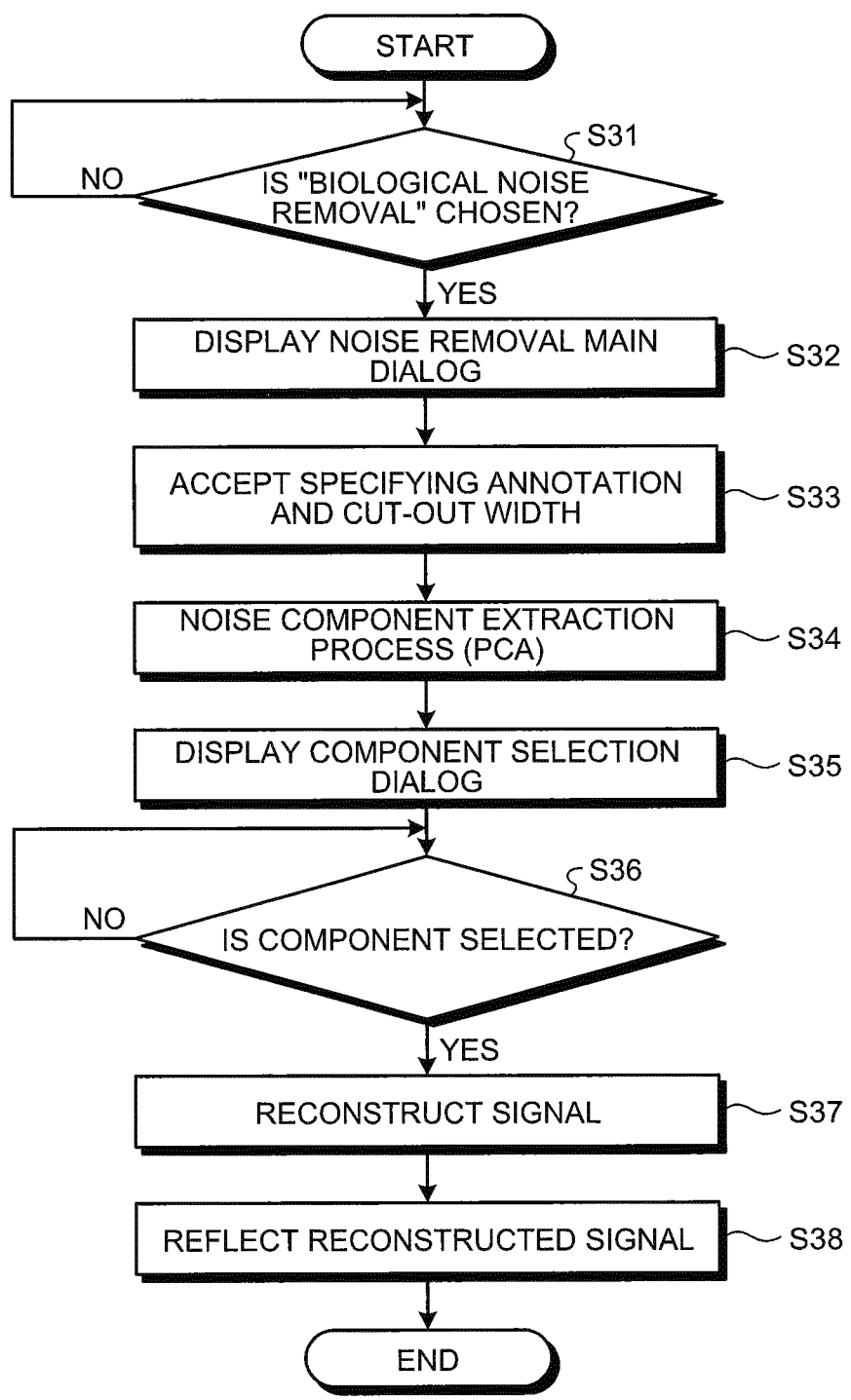
FIG. 18 is a flowchart schematically illustrating a flow of a noise removal process in the information display process at the stage of analysis.

FIG. 18 is a flowchart schematically illustrating the flow of the noise removal process in the information display process at the stage of analysis that is performed by the information display device 50. The analyzer properly determines the timing at which the noise removal process is executed. Specifically, the analyzer may perform the process when determining that a noise is mixed in a waveform at the timing right after the display of the analysis screen 206 and or may perform the process after the signal source is estimated and when the estimation result is not favorable.

As illustrated in FIG. 18, the information display device 50 determines whether "biological noise removal" is chosen from a menu on the analysis screen 206 (S31).

When the information display device 50 (a given waveform display unit 251d, an adjustment unit 251e, a waveform display unit 251f (see FIG. 26)) determines that "biological noise removal" is chosen from the menu on the analysis screen 206 (YES at S31), the information display device 50 displays a noise removal main dialog 300 (see FIG. 19) (S32) and accepts specifying an annotation and a cut-out width before and after the annotation.

Figure 19:
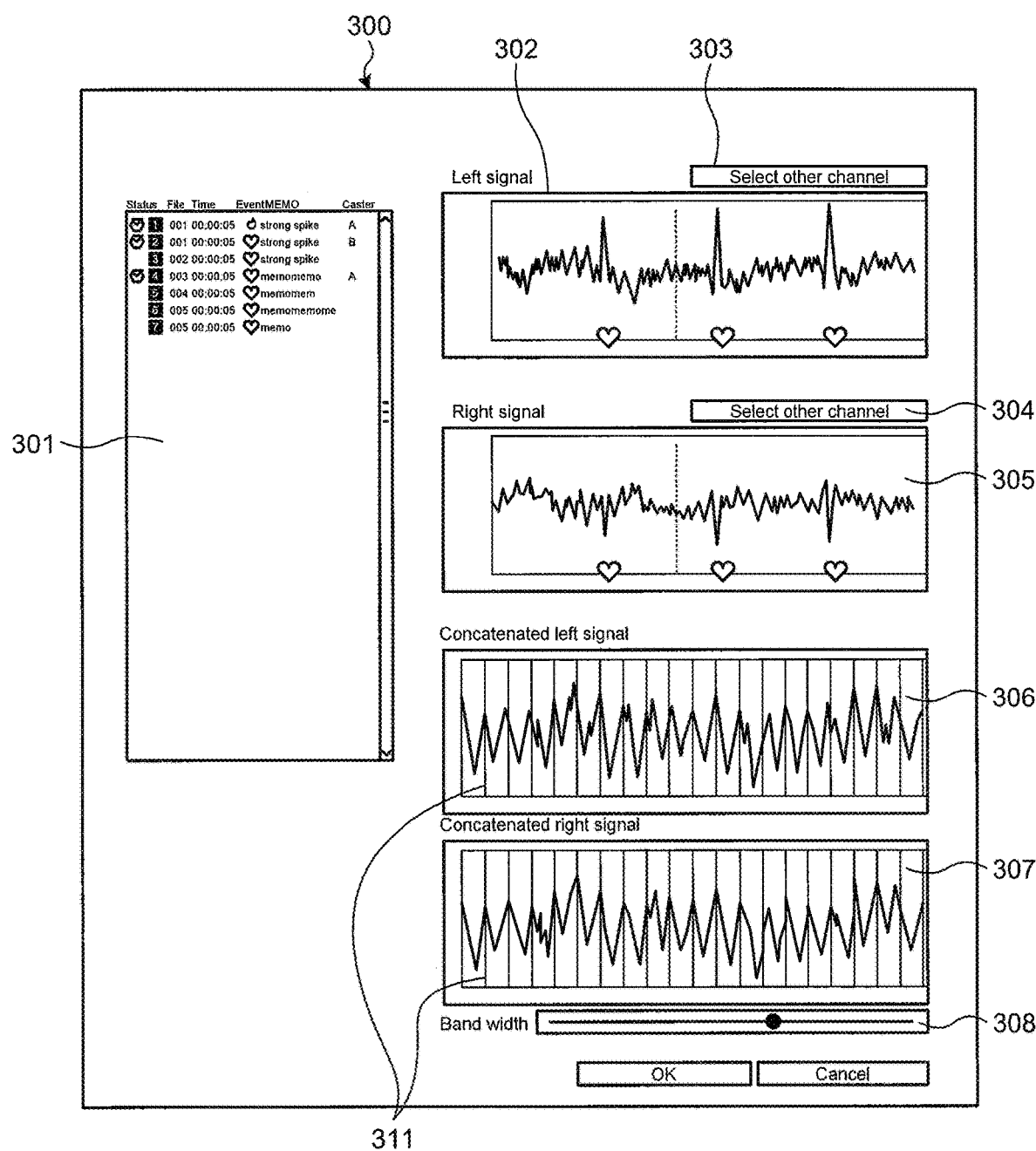
FIG. 19 is a front view illustrating an exemplary noise removal main dialog.

FIG. 19 is a front view illustrating the exemplary noise removal main dialog 300. As illustrated in FIG. 19, the information display device 50 (a list display unit 251*g* (see FIG. 26)) displays an annotation list 301 that is a list of signal waveforms in each of which a given waveform occurs in the noise removal main dialog 300 displayed on the monitor display 26 of the information display device 50. The same operation as that to make a display (scrolled/enlarged/downsized) in the annotation list 180 illustrated in FIG. 7 is performed on the annotation list 301. In the noise reduction process, as the time of noise is determined by the annotation, the annotation types displayed on the annotation list 180 may be limited to noire-related ones.

The information display device 50 (the waveform display unit 2510 displays a waveform display screen 302 and a waveform display screen 305 in the noise removal main dialog 300. The waveform display screen 302 displays EEG waveforms before and after the annotation of the channel that is selected on the annotation list 301. In the initial state, the waveform display screen 302 displays a signal the closest to the left ear of the subject (left signal). This is because a cardiac magnetic field noise that is a magnetic field generated by the heart is easily measured by the left and right sensors on the head sides by MEG. Needless to say, another channel may be used for the initial value according to the noise type to be dealt with. Furthermore, with a button 303, it is possible to switch the channels to be displayed on the waveform display screen 302.

When the waveform display screen 302 contains the annotation time, a display is made such that the annotation time (the time at which the given waveform occurs) is recognizable. According to FIG. 19, the information display device 50 displays heart-shaped (red) signs at the positions of annotation times.

The waveform display screen 305 displays MEG waveforms before and after the channel annotation that is selected on the annotation list 301. The waveform display screen 305 displays a signal (right signal) of a channel the closest to the right ear of the subject in the initial state. A button 304 enables the waveform display screen 305 to switch the displayed channel. The waveforms displayed on the waveform display screen 302 and the waveform display screen 305 may be electrocardiographic waveforms of an external device, such as an electrocardiograph.

The information display device 50 is also able to additionally specify (create) an annotation on the waveform display screen 302 or the waveform display screen 305 of the noise removal main dialog 300. An annotation that is specified on the waveform display screen 302 or the waveform display screen 305 is reflected in the annotation list 301. The method of specifying an annotation on the waveform display screen 302 or the waveform display screen 305 is the same method as that on the annotation list 180 illustrated in FIG. 7.

When an annotation relating to a noise is selected on the annotation list 301, the information display device 50 does not display other annotations. The information display device 50 leaves only the annotation on which the noise removal is to be performed in the list finally and performs the following process on the annotation that is left.

The information display device 50 (the given waveform display unit 251*d*) displays concatenated waveform display screens 306 and 307 on the noise removal main dialog 300. The concatenated waveform display screens 306 and 307 display waveforms obtained by cutting out MEG waveforms (given waveforms) before and after the annotation from the signals that are displayed on the waveform display screens 302 and 305 and concatenating the waveforms. In the embodiment, the information display device 50 focuses on only the annotation time and displays MEG waveforms before after the annotation time. As illustrated in FIG. 19, for easy understanding, the information display device 50 displays partition lines 311 that are given signs at the concatenated parts of the concatenated waveform (that is, with respect to each annotation).

The information display device 50 (the adjustment unit 251*e*) is able to adjust the cut-out width before and after the annotation that is displayed on the concatenated waveform display screens 306 and 307. As illustrated in FIG. 19, the cut-out width before and after the annotation displayed on the concatenated waveform display screens 306 and 307 are adjustable with a slider 308. In the case of cardiac magnetic field noise, mountains (or valleys) are seen. For this reason, the analyzer adjusts the cut-out width before and after the annotation time with the slider 308 such that the mountain (or valley) is within each range. The information display device 50 (the given waveform display unit 251*d*) changes the concatenated waveforms on the concatenated waveform display screens 306 and 307 according to the move of the slider 308. In other words, the slider 308 specifies, with respect to the time before and after the annotation, how much time is subjected to component extraction process (PCA) to be described below.

Figure 20A:
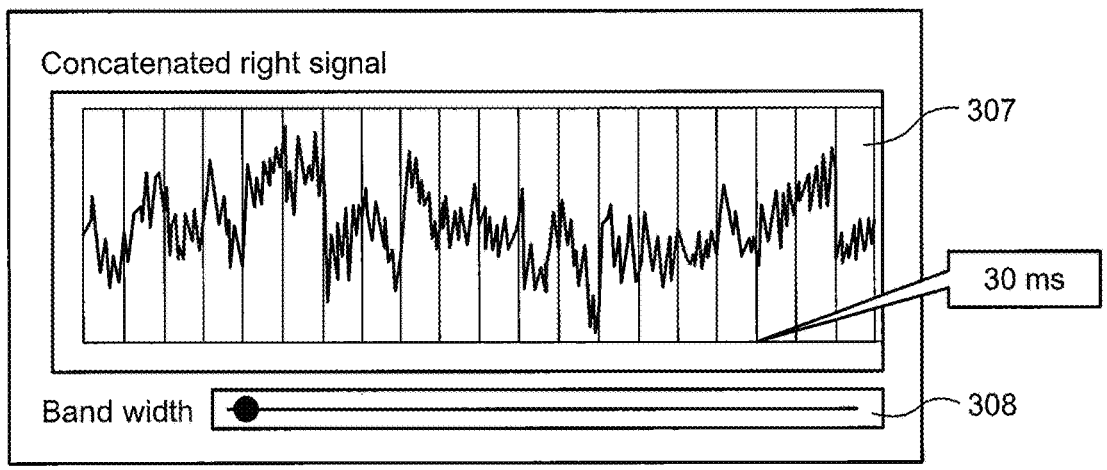
FIG. 20A is a diagram illustrating exemplary adjustment of a display area with a slider.
Figure 20B:
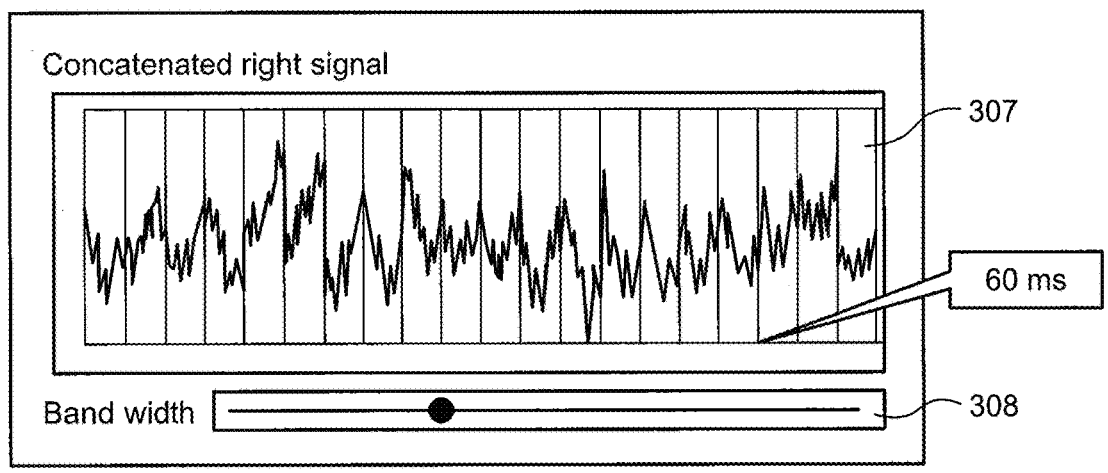
FIG. 20B is a diagram illustrating exemplary adjustment of the display area with a slider.
Figure 20C:
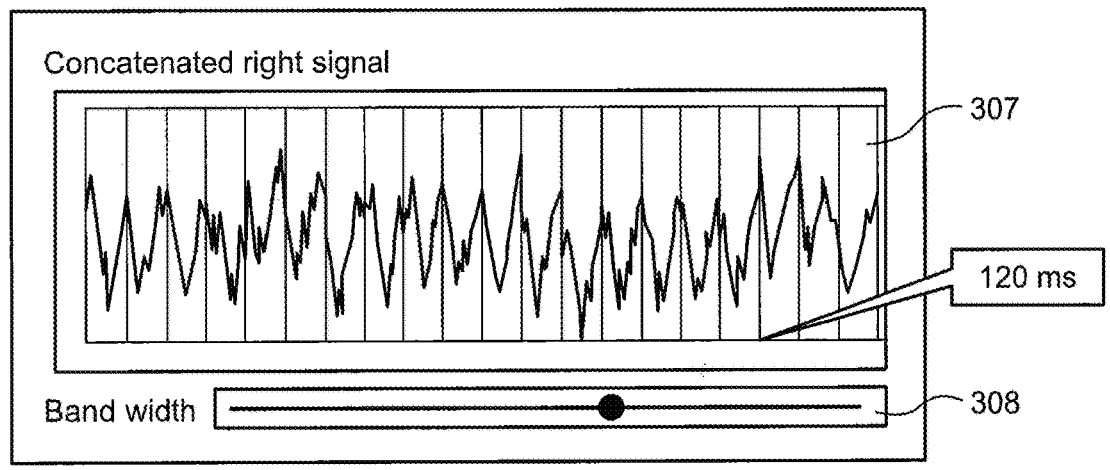
FIG. 20C is a diagram illustrating exemplary adjustment of the display area with a slider.

FIGS. 20A to 20C are diagrams illustrating exemplary adjustment of a display area with the slider 308. FIG. 20A is a diagram illustrating the case where the cut-out width is small (the width is insufficient). FIG. 20A illustrates the cut-out width adjusted at 30 ms with the slider 308. According to the example in FIG. 20A, the valleys of the cardiac magnetic field noise are not seen. In other words, according to the example in FIG. 20A, there is a risk that an accurate time of cardiac magnetic field noise is not contained.

FIG. 20B is a diagram illustrating the case where the cut-out width is intermediate (the width is slightly insufficient). FIG. 20B illustrates the cut-out width adjusted at 60 ms with the slider 308. According to the example in FIG. 20B, the valleys of the cardiac magnetic field noise are unclear.

FIG. 20C is a diagram illustrating the case where the cut-out width is large (the case where the width is preferable). FIG. 20C illustrates the cut-out width adjusted at 90 ms with the slider 308. According to the example in FIG. 20C, the valleys of the cardiac magnetic field noise are seen and the accurate time of cardiac magnetic field is contained.

By displaying concatenated waveforms on the concatenated waveform display screens 306 and 307 while adjusting the cut-out width before and after the annotation with the slider 308, the analyzer is able to cut out a signal containing the time of cardiac magnetic field easily and without fail.

On the concatenated waveform display screens 306 and 307, the lines each representing the cut-out area are displayed together with the concatenated waveforms; however, another display method may be employed as long as it is a mode where each of the cut-out waveforms can be checked simultaneously.

Figure 21:
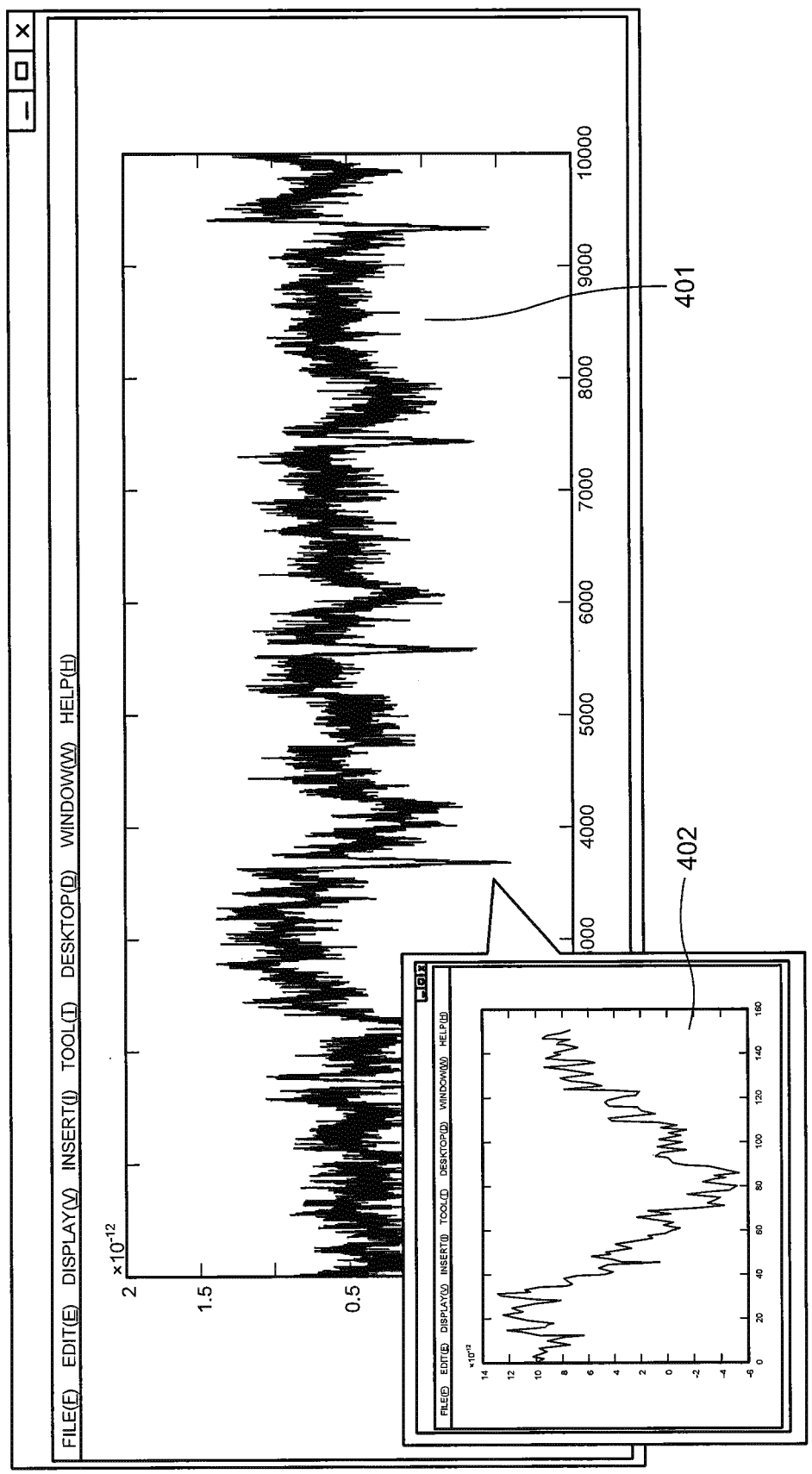
FIG. 21 is a diagram illustrating an exemplary error in specifying a noise time.

The necessity of adjusting the cut-out width before and after the annotation time will be described. Some noises appear at a given cycle as a cardiac magnetic field noise does. When such a noise is searched for, it is preferable to display a waveform at a resolution enabling checking the cycle. FIG. 21 is a diagram illustrating an exemplary error in specifying a noise time. When a waveform is represented at the resolution illustrated in 401 in FIG. 21, periodic valleys are obvious and it is easily understood that the valleys are cardiac magnetic field noises also in consideration of the intervals. In other words, it is preferable that the user adds an annotation (click on the screen) at the resolution illustrated in 401 in FIG. 21.

As for actual signals, however, a waveform like that illustrated in 402 in FIG. 21 may be represented. In this case, when the analyzer specifies an annotation time on the resolution graph illustrated in 401 in FIG. 21, occurrence of a certain error is unavoidable.

Accordingly, in order to pass a signal containing a noise time to the noise removal process without fail, it is necessary to cut out a signal with a cut-out width from the anterior and posterior parts of the annotation time that is specified by the analyzer; however, there is a disadvantage that increasing the width such that the noise occurrence time is contained without fail makes it difficult to determine the noise characteristics and increases the time taken to perform the noise removal process.

In other words, it is required that the signal subjected to noise processing be a signal with a proper width before and after the annotation time. Both a too small width (without accurate noise time contained) and a too large width (causing difficulty in determining the noise characteristics and increasing the process time) make it difficult to perform the proper noise processing.

In this manner, the information display device 50 displays the noise removal main dialog 300 (S32) and accepts specifying an annotation and a cut-out width before and after the annotation (S33).

Then, as illustrated in FIG. 18, the information display device 50 (a component extraction unit 251*a* (see FIG. 26)) performs principal component analysis (PCA) to extract a requested component (supposed to be a noise) from the noise signal obtained at S33 (S34). Principal component analysis (PCA) will be described in detail below.

The information display device 50 according to the embodiment uses principal component analysis (PCA) as the component extraction process. According to principal component analysis (PCA), when the noise signal is cut out properly, the component representing the noise appears on the top. In the embodiment, the component extraction process is performed by principal component analysis (PCA); however, the process is not limited thereto and independent component analysis (ICA) may be used to perform the component extraction process.

Figure 22:
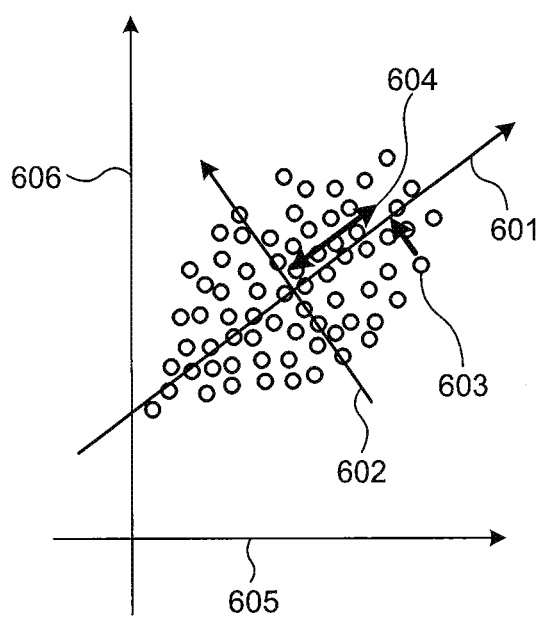
FIG. 22 is a diagram illustrating exemplary principal component analysis (PCA).

The principal component analysis (PCA) will be described briefly. FIG. 22 is a diagram illustrating exemplary principal component analysis (PCA). In FIGS. 22, 605 and 606 denote original axes and axes 601 and 602 are axes (components) obtained by principal component analysis (PCA). Principal component analysis (PCA) is a method performed on samples that are given to convert (rotate) the axes to easily compare the characteristics of the samples. Projecting the data of the given samples onto the axis 601 makes it easy to distinguish the samples from one another. Furthermore, the projection onto the axis 602 obtained at the top increases variation between the samples.

As in the embodiment, when the time widths before and after the annotation time are cut out, a sample that varies from a mountain (valley) point to another point is input to principal component analysis (PCA). In other words, samples from one whose noise is the largest to one whose noise reduces gradually are input. For this reason, when the value of each sample is projected onto the axis 601 representing the noise, the variation between the samples increases. In other words, the axis representing the noise component appears at the top.

As illustrated in FIG. 18, when the component extraction process (PCA) at S34 ends, the information display device 50 (a noise component selection unit 251*b* (see FIG. 26)) displays the noise removal component selection dialog (S35) and accepts selecting an axis (component) representing the noise on the noise removal component selection dialog (S36). When the axis (component) representing a noise is selected on the noise removal component selection dialog (YES at S36), the information display device 50 (a reconstruction unit 251*c* (see FIG. 26) reconstructs signals with respect to all channels according to the selection (S37).

By selecting the axis (component) representing a noise from the result of the principal component analysis (PCA), removing the components of the selected component, and reconstructing the signal, the information display device 50 acquires a signal without noise.

First of all, selecting the axis (component) representing a noise from the result of principal component analysis (PCA) will be described. Values obtained by projecting sets of data of respective samples onto the component are referred to as scores. In the case of the sample denoted by 603 in FIG. 22, 604 denotes the score of a first component (the values projected onto the first axis 601).

Figure 23:
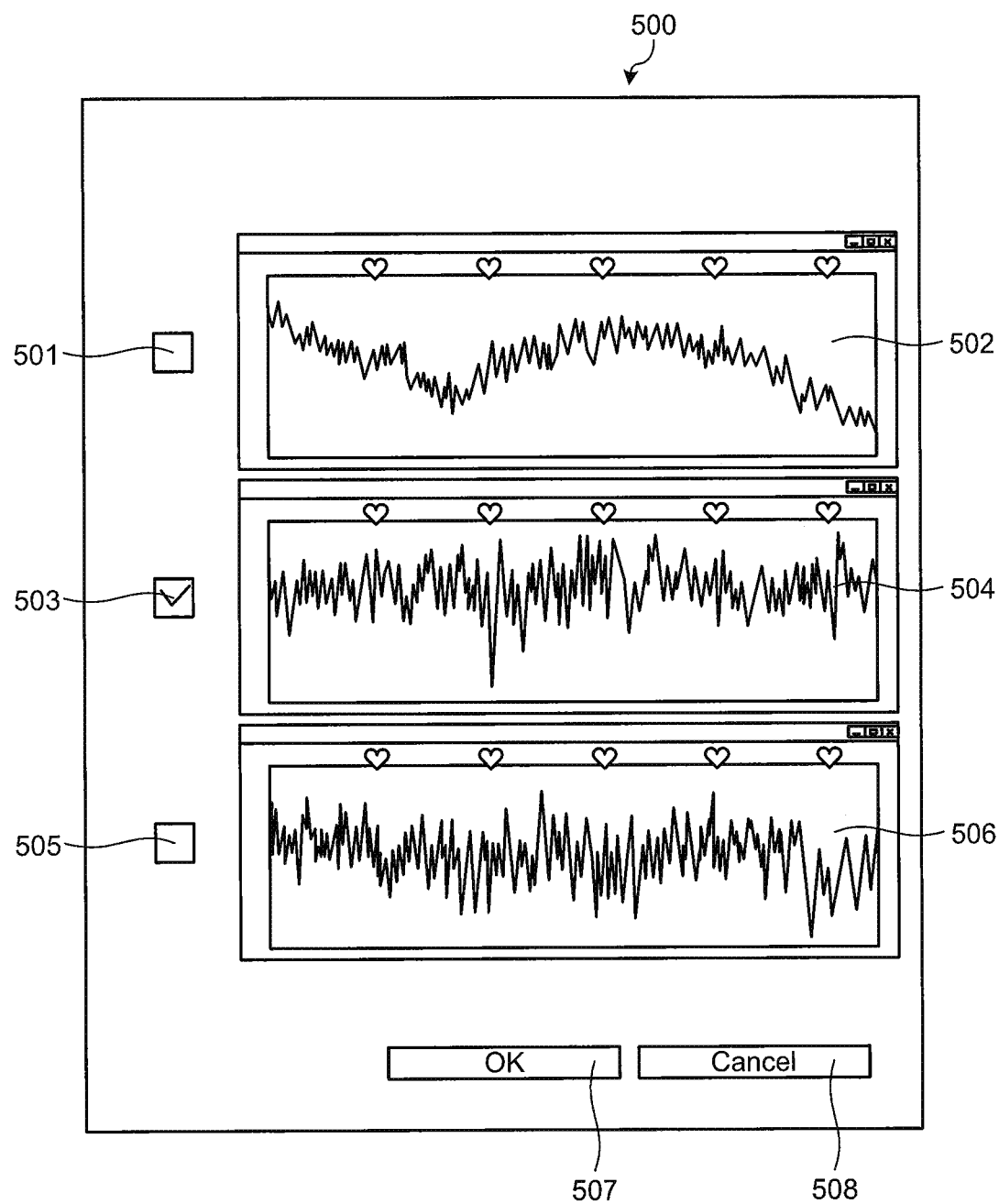
FIG. 23 is a front view illustrating an exemplary noise removal component selection dialog.

FIG. 23 is a front view illustrating an exemplary noise removal component selection dialog 500. As illustrated in FIG. 23, the noise removal component selection dialog 500 displayed on the monitor display 26 of the information display device 50 includes score display screens 502, 504 and 506. The noise removal component selection dialog 500 includes check boxes 501, 503 and 505 associated respectively with the score display screens 502, 504 and 506. The score display screens 502, 504 and 506 also display annotations (times). The noise removal component selection dialog 500 further includes an OK button 507 to determine selection of a component and a cancel button 508 to cancel selection of a component. The method of displaying annotations is the same as the display method of the noise removal main dialog 300. The number of score display screens to be displayed is not limited to three and the analyzer may change the number properly.

In the embodiment, the data of each time point serves as each sample. Thus, projecting the data about each time point onto the first component makes it possible to calculate scores on the first component. What obtained by displaying the calculated scores according to the respective time points is the score display screens 502, 504 and 506.

When the graphs displayed on the score display screens 502, 503 and 506 contain annotation times, displays are made such that the annotation times can be seen (times at which given waveforms occur). Heart-shaped (red) signs are displayed in the positions of the annotation times.

The score on the component representing the noise varies largely from a part where the noise is large to a part where the noise is small. In other words, the value increases (or decreases) at an annotation time (a time with a noise) and a significant change is seen between before and after the annotation time.

When the graphs displayed on the score display screens 502, 502 and 506 are viewed, the value significantly decreases on the score display screen 504 at the annotation times compared to those around the annotation times. On the other hands, no significant change are seen at the annotation times on the score display screens 502 and 506 and the components are not likely to be ones representing noises. As described above, representing annotation times on the graphs of the scores enables the analyzer to easily distinguish the component representing noises from other components.

In the case of the noise removal component selection dialog 500 illustrated in FIG. 23, the analyzer is able to determine that the score display screen 504 is a component representing noises by referring to the score of each component and the annotation times. On determining that the score display screen 504 is a noise component, the analyzer checks the check box 503 and presses the OK button.

Reconstructing a signal with respect to all channels according to the selecting at S36 will be described.

When an axis (component) representing noises is selected on the noise removal component selection dialog 500 and the OK button 507 is pressed, the information display device 50 performs a process to reconstruct a signal. The information display device 50 (the reconstruction unit 251c) excludes information about the component selected on the noise removal component selection dialog 500 and reconstructs a signal by using the scores of other components.

Figure 24:
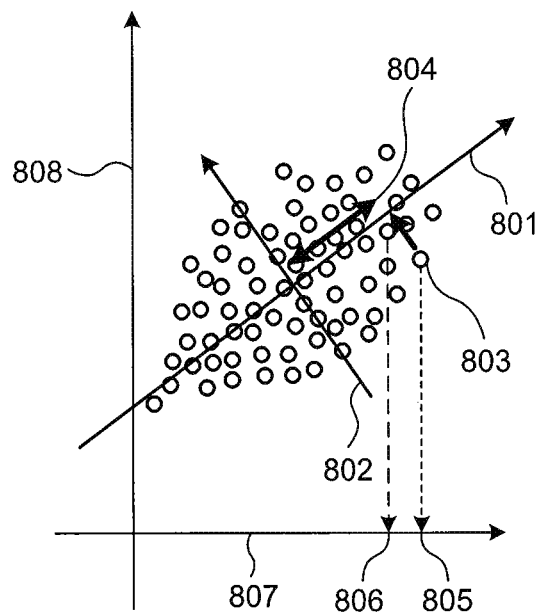
FIG. 24 is a diagram illustrating exemplary reconstruction of a signal corresponding to principal component analysis (PCA).

FIG. 24 is a diagram illustrating exemplary reconstruction of a signal according to principal component analysis (PCA). For simplicity, FIG. 24 illustrates the case where the number of sensors (the number of dimensions) is "2". In FIGS. 24, 807 and 808 denote the original axes (components) and axes 801 and 802 are axes (components) obtained by principal component analysis (PCA). The information display device 50 reconstructs a value with respect to the point of a sample 803. The original value of the sample 803 on the X-axis is 805.

As illustrated in FIG. 24, by projecting the sample 803 onto the axis 801 that is Component 1, the information display device 50 is able to calculate a score 804 (Score 1). In the same manner, as illustrated in FIG. 24, the information display device 50 is also able to calculate score 806 (Score 2) that is a value projected onto Component 2. Representing the sample 803 by using both Score 1 and Score 2 makes it possible to represent a set of coordinates of the same sample 803 as the original. By projecting the set of coordinates of the sample 803 onto the x-axis, the information display device 50 is able to calculate the original value 805 of the sample 803 on the X-axis as a value on the X-axis. In other words, the information display device 50 is able to reconstruct the same signal as the original by using the data of all the components.

Assume that Component 2 is specified by the analyzer as a component representing noise. In that case, Component 2 represents a noise component and thus is ignored on reconstruction. In other words, projection onto the axis 802 that is Component 2 is ignored and thus the sample 803 is represented as the score 804 on Component 1. The information display device 50 obtains the score 806 obtained by projecting the point 804 on Component 1 onto the X-axis as the signal that is reconstructed, ignoring the projection onto the axis 802 that is a noise component, that is, the signal from which the noise component is removed.

Finally, as illustrated in FIG. 18, the information display device 50 reflects the signals (signals from which noises are removed) with respect to all the channels that are reconstructed at S37 onto the analysis screen 206 serving as the main page (S38) and ends the noise removal process.

The reconstructed signals that are displayed on the analysis screen 206 serving as the main page (signals from which noises are removed) are used in the process at the latter stage, such as dipole estimation.

The information display device 50 (the reconstruction unit 251c) may further represent noise components based on a component representing noise that is selected on the noise removal component selection dialog 500. This allows the analyzer to view only cardiac magnetic field noises.

The information display device 50 will be described.

Figure 25:
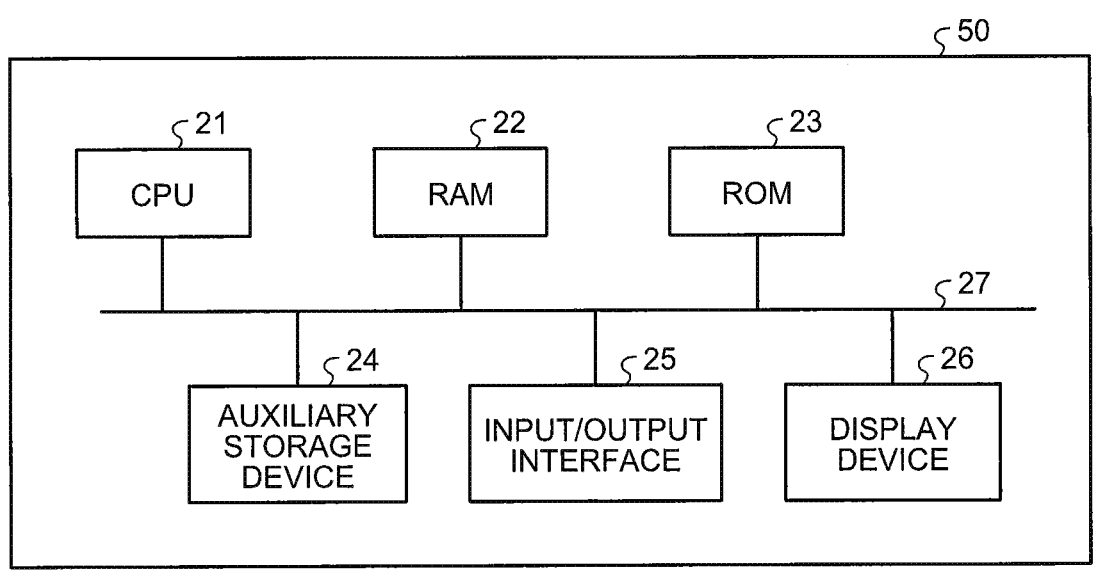
FIG. 25 is a hardware configuration diagram of an information display device.

FIG. 25 is a hardware configuration diagram of the information display device 50. The information display device 50 includes a CPU (Central Processing Unit: Processor) 21, a RAM (Random Access Memory) 22, a RAM (Read Only Memory) 23, an auxiliary storage device 24, an input/output interface 25, and a display device 26 that are connected with one another via a bus 27.

A CPU 21 controls entire operations of the information display device 50 and performs various information processes. The CPU 21 executes an information display program that is stored in a ROM 23 or the auxiliary storage device 24 to control operations for display on the measuring-recording screen 205 and the analysis screen 206. A RAM 22 is used as a work area of the CPU 21, and the RAM 22 may include a non-volatile RAM that stores main control parameters and information. The ROM 23 stores a basic input/output program. The information display program according to the invention may be saved in the ROM 23. The auxiliary storage device 24 is a storage device, such as a SSD (Solid State Drive) or a HDD (Hard Disk Drive) and, for example, stores a control program to control operations of the information display device 50 and various types of data and files necessary for operations of the information display device 50. The input/output interface 25 includes both a user interface, such as a touch panel, a keyboard, a display screen, or an operation button, and a communication interface that loads information from various sensors or the data recording server 42 and outputs analysis information to another electronic device. The display device 26 corresponds to the monitor display 26 in FIG. 1. The display device 26 displays the measuring-recording screen 205 and the analysis screen 206 and updates the screen according to the input and output operations via the input/output interface 25.

Figure 26:
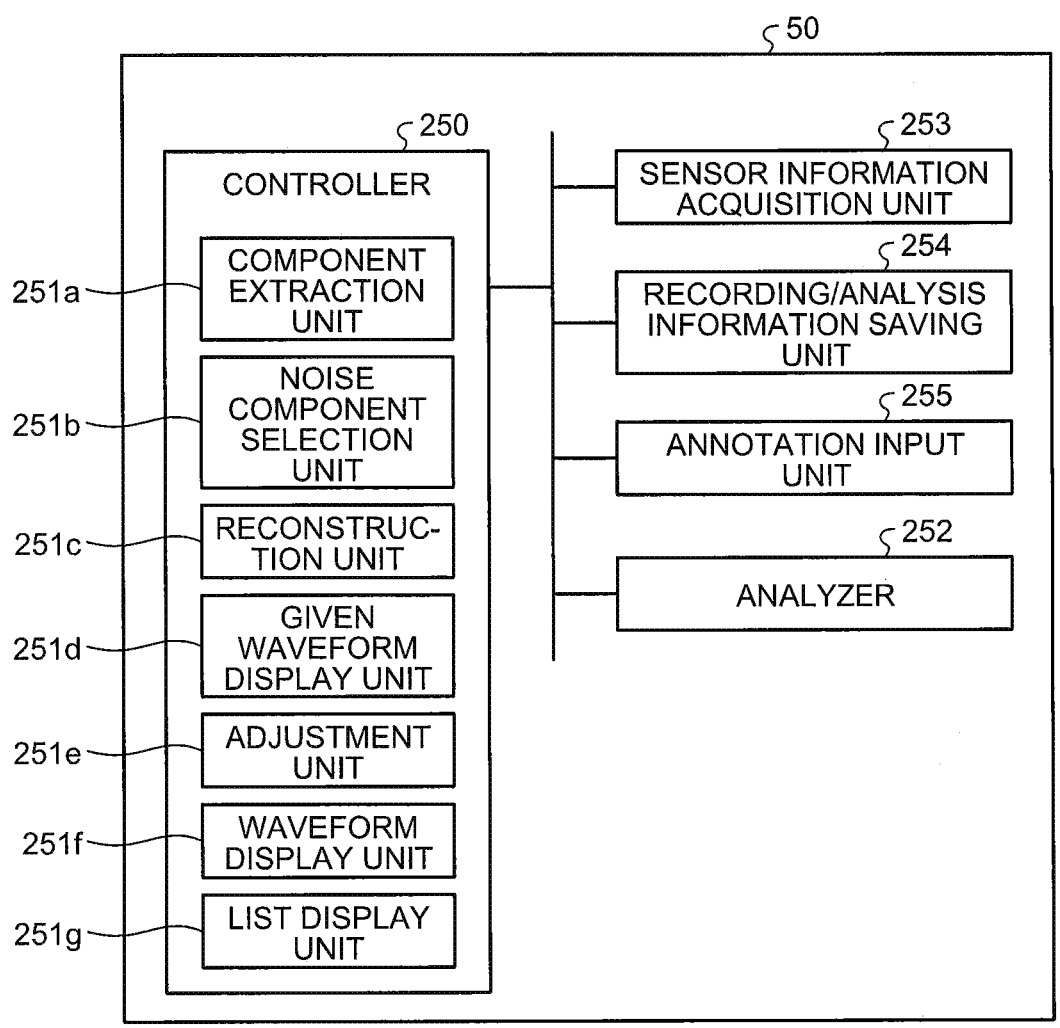
FIG. 26 is a functional block diagram of the information display device.

FIG. 26 is a functional block diagram of the information display device 50. The information display device 50 includes a controller 250, an analyzer 252, a sensor information acquisition unit 253, a recording/analysis information saving unit 254 and an annotation input unit 255. The controller 250 includes a display controller 251 that controls the screen display of the information display device 50.

The sensor information acquisition unit 253 acquires sensor information from the measurement device 3 or the data recording server 42. The annotation input unit 255 inputs annotation information added to the sensor information.

The analyzer 252 analyzes the collected sensor information. Analyzing sensor information includes analyzing signal waveforms, analyzing an amplitude singularity and analyzing brain magnetic fields containing the orientation of the current dipole.

The display controller 251 includes the component extraction unit 251a, the noise component selection unit 251b, the reconstruction unit 251c, the given waveform display unit 251d, the adjustment unit 251e, the waveform display unit 251f and the list display unit 251g. The display controller 251 controls the screen displays on measuring and recording and analysis on sensor information according to the method described with referent to FIGS. 2 to 24.

The recording/analysis information saving unit 254 saves the measurement data and the analysis result. When an annotation is added to the signal waveforms on measuring and recording, the annotation is saved in association with information about the time at which the signal waveforms are acquired.

The functions of the controller 250 including the display controller 251 are realized by the CPU 21 in FIG. 25. The functions of the analyzer 252 are realized by the CPU 21 and the RAM 22. The functions of the sensor information acquisition unit 253 and the annotation input unit 255 are realized by the input/output interface 25. The functions of the recording/analysis information saving unit 254 are realized by the ROM 203 or the auxiliary storage device 24.

When operations of the information display device 50 of the embodiment are realized by executing the information display program, the information display program causes the CPU 21 to execute (a) a procedure to display a signal detection time axis in a first direction of a displayed first display part screen that, (b) a procedure to display, in parallel, multiple waveforms acquired by measuring signals on a displayed second display part and in a second direction different from the first direction, and (c) a procedure to, when a spot on at least a waveform of the multiple signal waveforms or in an area in the vicinity of the waveform is specified on the second display part, display the spot in an enhanced manner and display a result of the specifying as specifying information in a time position on the first display part corresponding to the specified spot.

When the operations of the information display device 50 according to the embodiment are realized by executing the information display program, the information display program causes the CPU 21 to, when executing the noise removal process, execute a procedure to display the noise removal main dialog 300 and a procedure to display the noise removal component selection dialog 500.

Installing such an information display program in the information display device 50 makes it possible to easily check by sight a position or a range (area) of interest on a screen on which multiple signal waveforms are displayed on the same time axis.

As described above, the embodiment implements extracting a requested component from multiple given waveforms that are cut out of multiple signal waveforms based on detected biological signals and, while referring to the display of the time of occurrence of the given waveforms, accepting selecting an extraction result as a noise component from multiple extraction results. Accordingly, without any external device, it is possible to extract a noise signal from a complicated signal in which a signal to be acquired and the noise signal are mixed and enable confirmation that the noise removal process is optimum.

Furthermore, it is possible to provide a UI (User Interface) for an analyzer to cut out noise waveforms optimally not from separate waveforms obtained by using an external device but from waveforms of measured magnetic fields.

Figure 27:
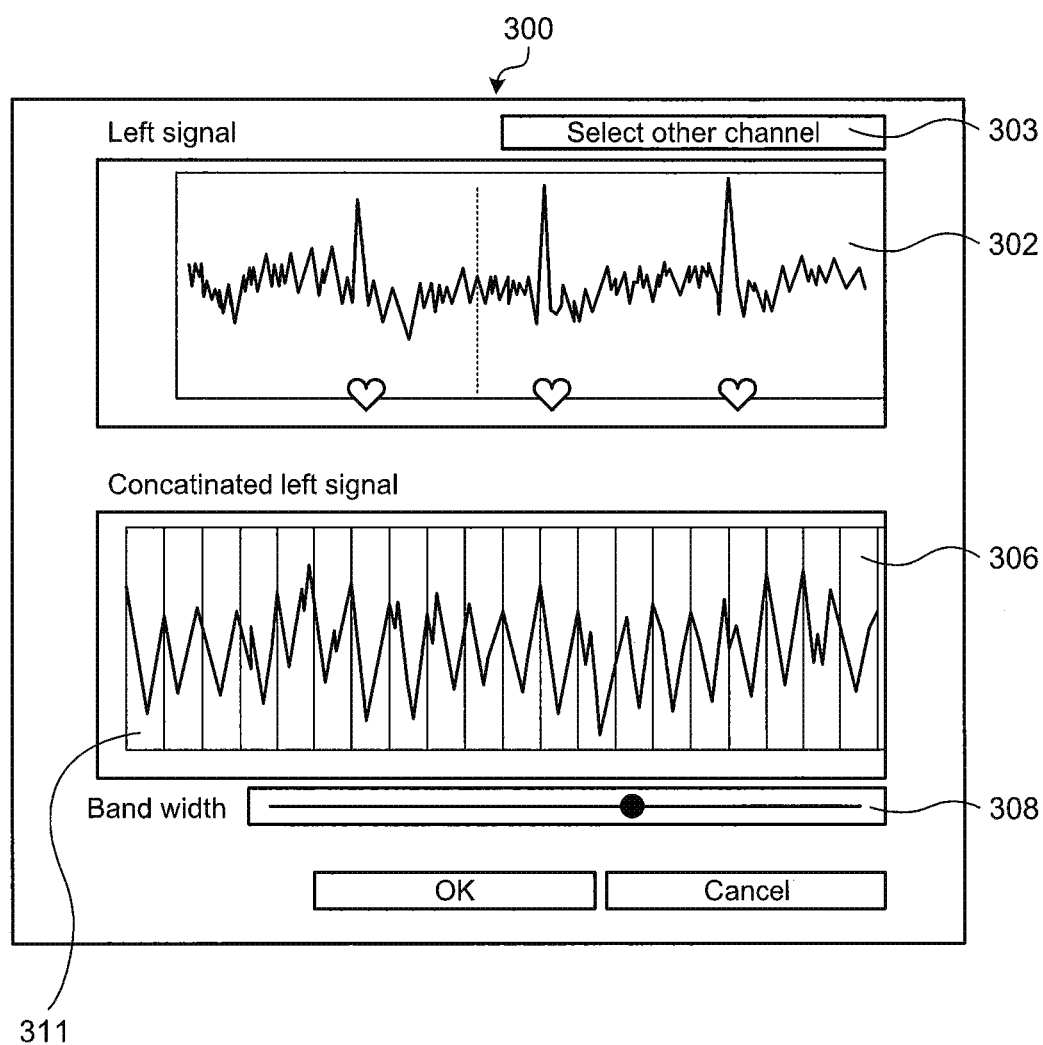
FIG. 27 is a diagram illustrating a modification of a display layout of the noise removal main dialog. The accompanying drawings are intended to depict exemplary embodiments of the present invention and should not be interpreted to limit the scope thereof. Identical or similar reference numerals designate identical or similar components throughout the various drawings.

FIG. 27 is a diagram illustrating a modification of the display layout of the noise removal main dialog 300. As illustrated in FIG. 27, the noise removal main dialog 300 need not include the annotation list 301 illustrated in FIG. 19 under the condition that annotations are narrowed down in advance. The noise removal main dialog 300 may include only the waveform display screen 302 to display a signal (left signal) the closet to the left ear of a subject in the initial state and the concatenated waveform display screen 306 to display a concatenated waveform based on the signal displayed on the waveform display screen 302.

In the above-described embodiment, the measurement device 3 is configured to collect MEG signals and EEG signals; however, the measurement device 3 is not limited thereto. For example, the measurement device 3 may collect MEG signals, an EEG different from the measurement device 3 may collect EEG signals, and the respective sets of biological signals may be output from the measurement device 3 and the EEG to the data recording server 42.

INDUSTRIAL APPLICABILITY

The information display technology of the invention is applicable to not only EEG and MEG parallel display but also a scene with, for example, an electrocardiograph or a spinal magnetometer where a large number of electrocardiographic waveforms and nerve signals are displayed on the same time axis.

The information display technology is also applicable to the case where signal waveforms that are collected from a geological exploration system that analyzes magnetic fields with a large number of geomagnetic sensors of a large number of convection meters (heat flow sensors) or a large number of dew meters (humidity sensors) that are set in the field of quality management are displayed on the same time axis. The information display technology of the invention is applicable to, not only brain waves, noises superimposed onto brain waves, a noise removal process, and display of a result but also a scene where multiple given waveforms are picked up from among a signal.

The above-described embodiment and modifications are illustrative and do not limit the present invention. Thus, numerous additional modifications and variations are possible in light of the above teachings. For example, at least one element of different illustrative and exemplary embodiment herein may be combined with each other or substituted for each other within the scope of this disclosure and appended claims. Further, features of components of the embodiment, such as the number, the position, and the shape are not limited the embodiment and thus may be preferably set. It is therefore to be understood that within the scope of the appended claims, the disclosure of the present invention may be practiced otherwise than as specifically described herein.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, nonvolatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

REFERENCE SIGNS LIST

1 Biological signal measurement system
3 Measurement device

20 Information display device
26 Monitor display
42 Data recording server
101 to 103 Display unit
103a Mark
106 Attribute icon
110, 120 Display unit
110a Annotation
112, 122 Time axis
115 Pop-up window
180 Annotation list
200 Enlarged display part
201A Area on the left in measuring-recording screen
201B Area on the right in measuring-recording screen
202A Area on the left in analysis screen
202B Area on the right in analysis screen
203A Area on the left in analysis screen
203B Area on the right in analysis screen
250 Controller
251 Display controller
251a Component extraction unit
251b Noise component selection unit
251c Reconstruction unit
251d Given waveform display unit
251e Adjustment unit
251f Waveform display unit
251g List display unit

CITATION LIST

Patent Literature

PTL 1: Japanese Laid-open Patent Publication No. 2009-195571

The invention claimed is:

1. An information display device comprising:
memory having computer readable instructions stored thereon; and
at least one processor configured to execute the computer readable instructions to cause the information display device to,
receive a request for component extraction from multiple signal waveforms corresponding to a plurality of detected biological signals,
extract the requested components from the multiple signal waveforms, the extracting the requested components including cutting out the requested components from the multiple signal waveforms,
display a noise removal component selection screen based on the extracted component, the noise removal component selection screen including portions of each signal waveform of the multiple signal waveforms corresponding to the multiple extracted components,
receive a user input on the noise removal component selection screen, the user input indicating a selection of a component from the multiple extracted components as a noise component of the multiple signal waveforms,
reconstruct the multiple signal waveforms by removing the selected noise component, the removing the selected noise component including sampling the portions of each signal waveform of the multiple signal waveforms corresponding to the multiple extracted components, displaying the sampled portions as points on a multi-axis graph, each axis of the multi-graph corresponding to a component of the multiple extracted components, and projecting the sampled points onto each of the multi-axis graph except for the axis corresponding to the selected noise component, the reconstructing including concatenating a portion of each signal waveform prior to the extracted noise component to a portion of each signal waveform after the extracted noise component, and
display the reconstructed multiple signal waveforms and times at which the reconstructed multiple signal waveforms occur.

2. The information display device according to claim 1, wherein the at least one processor further causes the information display device to:
reconstruct the multiple signal waveforms by removing the selected noise component based on a desired time window for the selected noise component.

3. The information display device according to claim 2, wherein the at least one processor further causes the information display device to:
receive a second user input indicating an adjustment of the desired time window.

4. The information display device according to claim 1, wherein the at least one processor further causes the information display device to:
extract the requested components by performing principal component analysis or independent component analysis on the multiple signal waveforms; and
display times at which the multiple signal waveforms occur based on a component score of each extracted component.

5. The information display device according to claim 1, wherein the at least one processor further causes the information display device to:
adjust a cut-out width of the multiple signal waveforms, the cut-out width being a time window to extract from the multiple signal waveforms;
cut out the portion of each signal waveform of the multiple signal waveforms corresponding to the time window based on the adjusted cut-out width; and
display the cut-out multiple signal waveforms.

6. The information display device according to claim 5, wherein the at least one processor further causes the information display device to:
display a given sign at a concatenated part in the reconstructed multiple signal waveforms.

7. The information display device according to claim 5, wherein the at least one processor further causes the information display device to:
display the multiple signal waveforms prior to the cutting-out of the selected noise components from the multiple signal waveforms.

8. The information display device according to claim 7, wherein the at least one processor further causes the information display device to:
display times at which the multiple signal waveforms occur together with the multiple signal waveforms prior to the cutting-out of the selected noise components from the multiple signal waveforms.

9. The information display device according to claim 7, wherein the at least one processor further causes the information display device to:
display an individual signal waveforms corresponding to a given channel in which the multiple signal waveforms tend to occur.

10. The information display device according to claim 1, wherein the at least one processor further causes the information display device to:
display a list of individual signal waveforms in which the multiple signal waveforms occur.

11. A biological signal measurement system comprising:
a measurement device configured to measure a subject on which measurement is performed and detect a biological signal; and
the information display device according to claim 1, the information display device configured to accept the biological signal that is detected by the measurement device.

12. A non-transitory computer-readable recording medium that contains at least one computer program, which when executed by a computer, causes the computer to:
receive a request for component extraction from multiple signal waveforms corresponding to a plurality of detected biological signals;
extract the requested components from the multiple signal waveforms, the extracting the requested components including cutting out the requested components from the multiple signal waveforms;
display a noise removal component selection screen based on the extracted component, the noise removal component selection screen including portions of each signal waveform of the multiple signal waveforms corresponding to the multiple extracted components;
receive a user input on the noise removal component selection screen, the user input indicating a selection of a component from the multiple extracted components as a noise component of the multiple signal waveforms;
reconstruct the multiple signal waveforms by removing the selected noise component, the removing the selected noise component including sampling the portions of each signal waveform of the multiple signal waveforms corresponding to the multiple extracted components, displaying the sampled portions as points on a multi-axis graph, each axis of the multi-axis graph corresponding to a component of the multiple extracted components, and projecting the sampled points onto each axis of the multi-axis graph except for the axis corresponding to the selected noise component, the reconstructing including concatenating a portion of each signal waveform prior to the extracted noise component to a portion of each signal waveform after the extracted noise component; and
display the reconstructed multiple signal waveforms of and times at which the reconstructed multiple signal waveforms occur.

13. The non-transitory computer-readable recording medium according to claim 12, wherein the computer is further caused to:
reconstruct the multiple signal waveforms by removing the selected noise component based on a desired time window for the selected noise component.

14. The non-transitory computer-readable recording medium according to claim 12, wherein the computer is further caused to:
extract the requested components by performing principal component analysis or independent component analysis on the multiple signal waveforms; and
display times at which the multiple signal waveforms occur based on a component score of each extracted component.

15. The non-transitory computer-readable recording medium according to claim 12, wherein the computer is further caused to:
adjust a cut-out width of the multiple signal waveforms, the cut-out width being a time window to extract from the multiple signal waveforms;
cut out the portion of each signal waveform of the multiple signal waveforms corresponding to the time window based on the adjusted cut-out width; and
display the cut-out multiple signal waveforms.

16. The information display device according to claim 1, wherein the multiple signal waveforms include a plurality of magneto-encephalogram signals.

17. The information display device according to claim 16, wherein the multiple signal waveforms further include a plurality of electro-encephalogram signals.

18. The information display device according to claim 1, wherein the at least one processor further causes the information display device to:
receive a plurality of annotation inputs on the plurality of detected biological signals from a user;
filter the plurality of annotation inputs, the filtering including removing non-noise related annotation inputs from the plurality of annotation inputs; and
display the filtered plurality of annotation inputs.

19. The non-transitory computer-readable recording medium according to claim 12, wherein the multiple signal waveforms include a plurality of magneto-encephalogram signals and a plurality of electro-encephalogram signals.

20. The non-transitory computer-readable recording medium according to claim 12, wherein the computer is further caused to:
receive a plurality of annotation inputs on the plurality of detected biological signals from a user;
filter the plurality of annotation inputs, the filtering including removing non-noise related annotation inputs from the plurality of annotation inputs; and
display the filtered plurality of annotation inputs.

* * * * *